US009718894B2

(12) United States Patent
Choi et al.

(10) Patent No.: US 9,718,894 B2
(45) Date of Patent: Aug. 1, 2017

(54) BIOPROCESSING DEVICE

(71) Applicant: Industry-University Cooperation Foundation Sogang University, Seoul (KR)

(72) Inventors: Jeong-Woo Choi, Seoul (KR); Taek Lee, Seoul (KR); Jun Hong Min, Seoul (KR)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 67 days.

(21) Appl. No.: 14/046,154

(22) Filed: Oct. 4, 2013

(65) Prior Publication Data

US 2015/0005479 A1 Jan. 1, 2015

(30) Foreign Application Priority Data

Jul. 1, 2013 (KR) ........................ 10-2013-0076712

(51) Int. Cl.

| | |
|---|---|
| ***C12Q 1/68*** | (2006.01) |
| ***B82Y 10/00*** | (2011.01) |
| ***B82Y 30/00*** | (2011.01) |
| ***H01L 51/00*** | (2006.01) |
| ***C12N 9/00*** | (2006.01) |
| ***C07K 19/00*** | (2006.01) |
| ***G11C 11/56*** | (2006.01) |
| ***G11C 13/00*** | (2006.01) |
| ***C07K 14/21*** | (2006.01) |

(52) U.S. Cl.

CPC .............. *C07K 19/00* (2013.01); *C07K 14/21* (2013.01); *G11C 11/56* (2013.01); *G11C 13/0019* (2013.01)

(58) Field of Classification Search

CPC ........... C12Q 1/6825; C12Q 2563/113; C12Q 1/6818; C12Q 2565/101; C12Q 2525/197; C12Q 1/6813; C12Q 2565/501; C12Q 2537/143; C12Q 1/00; B82Y 30/00; B82Y 15/00; B82Y 35/00; B82Y 10/00; G01N 27/3275; G01N 2035/0015

See application file for complete search history.

(56) References Cited

U.S. PATENT DOCUMENTS

2009/0123467 A1* 5/2009 Bedi et al. ................. 424/134.1

OTHER PUBLICATIONS

Williams et al. ("Williams", Curr. Protoc Nucleic Acid Chem. 2010, 1-29).*

Choi, "Electrochemical-type bioprocessing device composed of recombinant biomolecules," PRiME Pacific Rim Meeting on Electrochemical and Solid-State Science. Honolulu, Hawaii (2012) (4 pages).

Lee et al., "Multifunctional DNA-based biomemory device consisting of ssDNA/Cu heterolayers," Biosens Bioelectron. 26(5):2304-10 (2011).

Yagati et al., "Multi-bit biomemory consisting of recombinant protein variants, azurin," Biosens Bioelectron. 24(5):1503-7 (2009).

Yagati et al., "Write-Once-Read-Many-Times (WORM) biomemory device consisting of cysteine modified ferredoxin," Electrochem Commun. 11:854-8 (2009).

Yoo et al., "Bioprocessing device based on protein/DNA biohybrid material," 2013 MRS Spring Meeting & Exhibit. San Francisco, CA (2013) (5 pages).

* cited by examiner

*Primary Examiner* — Misook Yu
*Assistant Examiner* — Kauser Akhoon
(74) *Attorney, Agent, or Firm* — Harness, Dickey & Pierce, P.L.C.

(57) ABSTRACT

Provided is a bioprocessing device including a hybrid of (1) a protein having a redox potential; and (b) a single strand DNA (ssDNA) conjugated to the protein. The bioprocessing device of the present invention has a function of information reinforcement, information regulation, or information amplification. This bioprocessing device of the present invention presents a new concept of biocomputing system enabling various functions.

18 Claims, 21 Drawing Sheets
(2 of 21 Drawing Sheet(s) Filed in Color)

(a) Case 1

(a)
(b)
(c)
Recombinant Azurin
Thiol-modified ssDNA
Azu/DNA
Potential (V) vs Ag/ AgCl
5.0
2.5
0
-2.5
-5.0
0.6
0.4
0.2
0
-0.2

(b)

| Input | RP (mV) | OP (mV) | Regulated Current (μC) |
|---|---|---|---|
| Mn | 305 ± 71 | 413 ± 47 | 0.37 ± 0.12 |
| Fe | 349 ± 52 | 374 ± 55 | 0.51 ± 0.13 |
| Co | 320 ± 59 | 350 ± 34 | 0.56 ± 0.28 |
| Zn | 246 ± 41 | 334 ± 52 | 1.59 ± 0.41 |
| Ni | 140 ± 22 | 437 ± 71 | 4.10 ± 0.59 |
| Cu | 106 ± 27 | 275 ± 34 | 1.33 ± 0.34 |

BIOPROCESSING DEVICE

CROSS-REFERENCE TO RELATED APPLICATIONS

This application claims priority from application no. 10-2013-0076712, filed Jul. 1, 2013, in the Republic of Korea. The prior application is incorporated herein by reference.

TECHNICAL FIELD

The present disclosure relates to a bioprocessing device.

BACKGROUND ART

The semiconductor industry has been growing at a rapid fast however the miniaturization of electronic devices has reached to its technological and physical limits such as component integration, heat, shorting of device, and efficiency. To overcome these current limitations molecular electronics enabled to approach the molecular-level size control, fabrication, replicate the silicon-based device functions. Alternatively, the current molecular electronics can be suited well to alter the current silicon-based electronic device. In recent years, molecular logic gates and computational devices has got much attention particularly the developments in biomolecular information processing systems by mimicking the inherent properties of enzymes towards realization of bioprocessing systems. Difficulties in developing circuits and the scaling-up complexity can be solved easily and naturally by application of biomolecular systems. The processing operations are performed by biochemical reactions that proceed in solutions or at functionalized interfaces. Since last decade, Choi's group has been focused on 'information storage device based on biomolecules'. Previous works demonstrates the basic memory functions such as storage, reading, and reset of the information performed by using metalloprotein-based biomemory device. Further, two different metalloproteins were coupled to demonstrate multi-leveled storage functions of protein based electrochemical biomemory. Also, biomemory devices with various functions have been developed to overcome the limitations of silicon-based memory device. However, these reported literatures only demonstrate basic information storage function also hard to perform the molecular-based computing owing to simple functionality.

Throughout the specification, a number of publications and patent documents are referred to and cited. The disclosure of the cited publications and patent documents is incorporated herein by reference in its entirety to more clearly describe the state of the related art and the present disclosure.

DISCLOSURE

Technical Problem

The present inventors endeavored to develop a bioprocessing device capable of overcoming limitations of molecular electronic devices. As a result, the present inventors first developed a novel bioprocessing device from simple metalloprotein-based biomemory devices, the bioprocessing device having a single hybrid molecule and enabling various functions, such as, "information reinforcement", "information regulation", and "information amplification", and then completed the present invention.

An aspect of the present invention is to provide a bioprocessing device.

Another aspect of the present invention is to provide a method for fabricating a bioprocessing device.

Other purposes and advantages of the present invention will become clarified by the following detailed description of invention, claims, and drawings.

According to an aspect of the present invention, there is provided a bioprocessing device including a hybrid of (a) a protein having a redox potential; and (b) a single strand DNA (ssDNA) conjugated to the protein.

The present inventors endeavored to, develop a bioprocessing device capable of overcoming limitations of molecular electronic devices. As a result, the present inventors first developed a novel bioprocessing device including a hybrid of a protein having a redox potential and a protein conjugated to the protein, from simple metalloprotein-based biomemory devices, the bioprocessing device having a single hybrid molecule and enabling various functions, such as, "information reinforcement", "information regulation", and "information amplification".

Here, one of the main characteristics of the present invention is to include a hybrid of the protein having a redox potential, which functions as a platform module, and the ssDNA, which functions as a signal receptor module.

According to one embodiment of the present invention, the protein having a redox potential is a recombinant protein in which a cysteine residue is introduced, the recombinant protein being directly immobilized onto a substrate through the cysteine residue.

The protein having a redox potential contains a cysteine residue introduced therein, and thus is self-assembled and directly immobilized onto a substrate.

According to one embodiment of the present invention, the protein is a metalloprotein. According to another embodiment of the present invention, the metalloprotein is azurin, hemoglobin, myoglobin, hemerythrin, cytochrome, iron-sulfur protein, rubredoxin, plastocyanin, ferritin, ceruloplasmin, carbonic anhydrase, vitamin $B_{12}$-dependent enzyme, nitrogenase, superoxide dismutase, chlorophyll-containing protein, calmoduline, glucose-6-phosphatase, hexokinase, DNA polymerase, vanabin, arginase, catalase, hydrogenase, iron-responsive element binding protein, aconitase, urease, cytochrome oxidase, laccase, alcohol dehydrogenase, carboxy peptidase, amino peptides, β-amyloid protein, nitrate reductase, glutathione peroxidase, metallothionein, or phosphatase. According to a certain embodiment of the present invention, the metalloprotein is azurin.

More specifically, the azurin is a protein having a redox potential. Azurin derived from microorganisms (e.g., *Pseudomonas aeruginosa*) is induced to contain a cysteine residue (e.g., Lys92Cys(K92C)) through site-specific mutagenesis, and thus is directly immobilized onto a gold substrate via a disulfide bond.

The ssDNA constituting the hybrid of the present invention is indirectly conjugated to the protein having a redox potential.

According to one embodiment of the present invention, the ssDNA of the present invention is modified with a thiol group, and conjugated to the protein having a redox potential via a linker. The linker of the present invention includes any linker known in the art, which can conjugate protein and DNA to each other. According to another embodiment of the present invention, the linker is sulfosuccinimidyl-4-(N-maleimidomethyl cyclohexane-1-carboxylate (SMCC), formaldehyde, 1-ethyl-3-[3-dimethylaminopropyl]carbodiimide hydrochloride (EDC), bis[beta-(4-azidosalicylamido)ethyl]

disulfide (BASED), or bis-maleimidohexane (BMH). According to a certain embodiment of the present invention, the linker is SMCC.

The hybrid of the present invention may be prepared by the following various methods.

(1) An amino group of a protein having a redox potential is reacted with a linker (e.g., sulfo-SMCC) to form an amide bond, and then thiol-modified ssDNA (sulfhydryl-containing biomolecule) is added thereto to react with a maleimide group of the recombinant azurin-linker to form a thioether bond, thereby preparing a recombinant azurin-ssDNA hybrid.

(2) Thiol-modified ssDNA (sulfhydryl-containing biomolecule) is reacted with a linker. A protein having a redox potential is added to the thiol-modified ssDNA linker to form an amide bond, thereby preparing a recombinant protein having a redox potential—ssDNA hybrid.

(3) Amine-modified ssDNA is reacted with a linker to form an amide bond. The recombinant azurin is treated with DTT for reducing cysteine residue of an azurin molecule, to prepare a protein having a redox potential. The protein having a redox potential is reacted with the amine-modified ssDNA-linker to form a thioether bond, thereby preparing a recombinant protein-ssDNA hybrid having redox potential.

(4) The recombinant azurin is treated with DTT for reducing cysteine residue of an azurin molecule. The protein having a redox potential is reacted with a linker to form a thioether bond. Amine-modified ssDNA is added thereto to prepare a protein having a redox potential—ssDNA hybrid.

According to one embodiment of the present invention, the hybrid is prepared by method (2) above.

According to one embodiment of the present invention, the ssDNA is in the 20-mer to 100-mer size range. According to another embodiment of the present invention, the ssDNA is in the 30-mer to 70-mer range. According to a certain embodiment of the present invention, the ssDNA is in the 40-mer to 60-mer size range.

The hybrid of the present invention is directly immobilized onto a substrate through the cysteine residue of the protein having a redox potential.

According to one embodiment of the present invention, the substrate may be made of metal, metal oxide, glass, ceramic, quartz, silicon, semiconductor, Si/$SiO_2$ wafer, germanium, gallium arsenide, carbon, carbon nanotubes, polymer, Sepharose, or agarose. According to another embodiment of the present invention, the substrate is a metal substrate, and according to a certain embodiment of the present invention, the substrate is a gold (Au) substrate.

The bioprocessing device of the present invention has specific oxidation and reduction potentials due to the protein having redox potential.

According to one embodiment of the present invention, the bio-memory device of the present invention is operated by application of reduction and oxidation potentials thereto.

The present invention is characterized in that a bioprocessing device can be applied as a nano-level information storage device by using electron transfer characteristics exhibited depending on the applied voltage, the bioprocessing device being fabricated by self-assembling a protein molecule, in which a thiol group, that is, cysteine residue is introduced, onto a surface of a substrate (e.g., a gold substrate) and conjugating the ssDNA to the protein via a linker.

When the protein-based bioprocessing device of the present invention is electrically operated, the bioprocessing device of the present invention is reversibly changeable and electrically readable. The bioprocessing device of the present invention may be constituted as follows. This electrical device includes a substrate. The substrate is as described above. In examples below, the substrate is an electrically charged substrate having a gold coated surface. A redox-active layer is formed on the substrate. In the present invention, a Self-Assembled Monolayer (SAM) of the cysteine-modified recombinant protein having a redox potential may be used as the redox-active layer. The redox-active layer is in a predetermined electronic state, for example, an oxidation state or a reduction state, by the recombinant protein. An electrode is connected to the redox-active layer. The device of the present invention includes an electric field source, for example, a voltage supply unit, connected to the substrate or the electrode, or both of the substrate and the electrode. A flow of electrons is induced by a voltage or an electron beam supplied by the electric field source, and thus memory characteristics are exhibited.

Therefore, in the case where the memory device of the present invention is electrically constructed, the device of the present invention includes (i) a substrate, (ii) an SAM of a cysteine-modified recombinant protein having a redox potential, which is immobilized on the substrate, as a redox-active layer (iii) an electrode connected to the redox-active layer, and (iv) an electric field source supplying a voltage or an electron beam to the substrate and/or the electrode.

Meanwhile, the present invention will be described with reference to specific examples, in which the bio-memory device of the present invention is electrochemically constructed, as follows.

The present invention is directed to an information storage device capable of changing oxidation and reduction states of the immobilized protein by electrochemically controlling the applied voltage. A substrate having a protein thin layer is placed in an electrolytic solution, for example, a HEPES electrolyte. The substrate is a working electrode, and connected to a potentiostat to be operated, and a reference electrode (e.g., Ag/AgCl) and a counter electrode (e.g., Pt) are inserted in the electrolyte. The reference electrode is used as a criterion for reading a potential change of the working electrode when the potentiostat sweeps the voltage. The counter electrode is used as a passage through which electrons flow by the potential control of the potentiostat. This 3-electrode system has been known as one of the most electrochemically constituted systems. The simple electrochemical system obtains a simple voltage-current curve through cyclic voltammetry. An open-circuit potential means that, in a voltage-free state, i.e., in a circuit-broken state, a system is constructed to have a potential difference due to intrinsic property of the protein layer and intrinsic property of the electrolyte, and naturally reaches the equilibrium state to have a specific potential. Based on the reverse use of this principle, a system can be artificially made close to the equilibrium state by applying an open-circuit potential to the system when the open-circuit potential is known. Specifically, when the protein accepts electrons from the electrolyte by application of a specific reduction potential to a protein thin layer, the open-circuit potential is applied thereto so that the protein thin layer returns to its natural equilibrium state and releases extra electrons. Conversely, even when the protein thin layer is oxidized by releasing the electrons, the open-circuit potential is applied thereto, so that the protein thin layer returns to its original potential state while electrons that have flown out from the protein thin layer again flow into the protein thin layer. That is, the open-circuit potential serves to read the oxidation or reduction state of the protein layer.

According to one embodiment of the present invention, the bioprocessing device further includes conductive nanoparticles, semi-conducting nanoparticles, or heavy metal ions. According to another embodiment of the present invention, a DNA sequence complementary to the ssDNA is coupled with the nanoparticles, so that the nanoparticles complementarily bind to the ssDNA constituting the bioprocessing device of the present invention. The heavy metal ions bind to the ssDNA through an ionic bond.

The bioprocessing device of the present invention has an information reinforcement function by including conductive nanoparticles.

As used herein, the term "information reinforcement" means a function capable of storing more electrons as compared with the conventional bio-memory device. More specifically, upon application of oxidation potential, the potential gives electron transfer from the Azu/DNA hybrid to the electrode, resulting in the storage of positive charges. This state may be regarded as a 'Write' state. The application of reduction potential enables to produce an outflow of electron transfer to the Azu/DNA hybrid, and this state may be regarded as an 'Erase' state. Application of oxidation potential and reduction potential and measurement of the current response are dependent on the resistance-capacitance (RC) time constant of the electrochemical system. As shown in FIG. 6*b*, the application of oxidation potential of 232 mV quantitatively oxidizes the Azu/DNA hybrid layer (Write state), resulting in the storage of positive charge in the hybrid, and the application of reduction potential of 83 mV converts the hybrid layer into its original state (Erase state). The reductive current had the same magnitude as the oxidation current. FIG. 6*c* shows results of validating functions of the conventional bio-memory device when two types of current responses of oxidation potential step of 232 mV and reduction potential step of 83 mV were applied to the azurin/DNA hybrid layer (FIG. 6*c*: black line). The information reinforcement function is similar to the conventional biomemory function. However, when the cDNA-GNP is added to the Azu/DNA hybrid, the charge storage capability is drastically enhanced in a defined area as compared with the conventional biomemory device (FIG. 6*c*: purple line).

The bioprocessing device of the present invention has an information regulation function by including heavy meal ions.

As used herein, the term "information regulation" means a function capable of evaluating various potentials depending on input materials (e.g., heavy metal). The ssDNA arm constituting the bioprocessing device of the present invention has a charged backbone that can bind to various heavy metal ions, such as Cu, Zn, Ni, Co, Fe, and Mn (FIG. 7*a*). The ssDNA has been shown to contain four potential sites for binding with metal ions: 1) negatively charged phosphate oxygen atoms, 2) ribose hydroxyl groups, 3) base rings, and 4) exocyclic base keto groups. During electron transfer, the interaction between DNA and the heavy metal ions plays an essential role in regulating and transferring electrochemical signals. Therefore, the ssDNA arm may be used as a regulation receptor, and the input material such as heavy metal ions may be regarded as a regulatory operator. In the cases where input materials are applied, oxidation potentials, reduction potentials, and regulated currents, which are specific to the input materials, are exhibited. This information regulation function can provide the application such as multi-bit biomemory.

The bioprocessing device of the present invention has an information amplification function by including semi-conducting nanoparticles.

As used herein, the term "information amplification" means that the bioprocessing device of the present invention can function as a solid-state biotransistor. More specifically, the capacitance (C1) and tunneling resistance (R1) of the protein having a redox potential (e.g., azurin)/ssDNA hybrid junction can be easily manipulated by changing the tip hybrid distance, which is usually achieved by controlling the STM bias (Vs) and current settings (Is). By varying the C1 value, the single electron charging energy (EC) can be modified dependently on the capacitance values, as well as the voltage distribution between the two junctions, which is determined by the capacitance ratio (V1/V2=C2/C1). Therefore, the bioprocessing device of the present invention shows a non-ohmic behavior, and behaves like a diode by applying a bias voltage from −0.5 to +0.5 V.

According to another aspect of the present invention, the present invention provides a method for fabricating the bioprocessing device of the present invention.

Since the method of the present invention is directed to a method for fabricating the bioprocessing device, descriptions of overlapping contents between the method and the bioprocessing device are omitted to avoid excessive complication of the specification due to repetitive descriptions thereof.

The bioprocessing device of the present invention presents a new concept of a biocomputing system capable of performing various functions.

Advantageous Effects

Features and advantages of the present invention are summarized as follows:

(1) The present invention provides a bioprocessing device and a method for fabricating the same.

(2) The bioprocessing device of the present invention has an information reinforcement, information regulation, or information amplification function.

(3) The bioprocessing device of the present invention represents a new concept of a biocomputing system capable of performing various functions.

DESCRIPTION OF DRAWINGS

The application file contains drawings executed in color (FIGS. 7*c*, 8*b* and 8*c*). Copies of this patent or patent application with the color drawing will be provided by the Office upon request and payment of the necessary fee.

FIG. 3*a* illustrates a bioprocessing mechanism; FIG. 3*b* illustrates structures and functions; FIG. 3*c* shows the results validating the biohybrid, FIG. 3*d* shows topography; and FIG. 3*e* shows surface analysis results by a Raman spectrometer.

FIG. 6*a* shows CV results of 1) an Azu/DNA hybrid and 2) an Azu/DNA-cDNA/GNP hybrid; FIG. 6*b* shows a Write or Erase state depending on the application of oxidation or reduction potential; and FIG. 6*c* shows results validating the conventional biomemory function by applying two types of current responses of oxidation and reduction potentials to the recombinant azurin/DNA hybrid layer. FIGS. 6*d* and 6*e* show schematic diagrams of oxidation potential, reduction potential, and current responses therefore. FIG. 6*f* shows memory performance maintained for 300 cycles.

FIG. 7*a* shows that an ssDNA arm has a charged backbone that can bind to various heavy metal ions, such as Cu, Zn, Ni, Co, Fe, and Mn; FIG. 7*b* shows values of oxidation potentials, reduction potentials, and regulated currents for various heavy metal ions; FIG. 7*c* shows potential variation values of Az/DNA hybrids to which various input materials such as heavy metal ions were added; and FIG. 7*d* shows regulated current variations depending on input of heavy metal ions.

FIG. 8*a* shows a set-up composition of scanning tunneling spectroscopy (STS) which is an effective tool for information amplification through Azu/DNA hybrid in a double-barrier tunnel-junction (DBTJ) configuration; and FIG. 8*b* shows that the Azu/DNA hybrid exhibits a non-ohmic behavior and behaves like a diode when a bias voltage from −0.5 to +0.5 V is applied to the Azu/DNA hybrid. FIG. 8*c* shows I-V characteristics of the Azu/DNA-cDNA/QD hybrid under the application of −2.0 to +2.0 V which shows electrical bistability; and FIG. 8*d* shows I-V characteristics of a monolayer of Az/DNA-cDNA/QD hybrid core-shell nanoparticles, measured with a Pt/Ir tip of an STM under two sweep voltage directions, under the application of 0-2-0 V.

BEST MODE

Figure 1A:
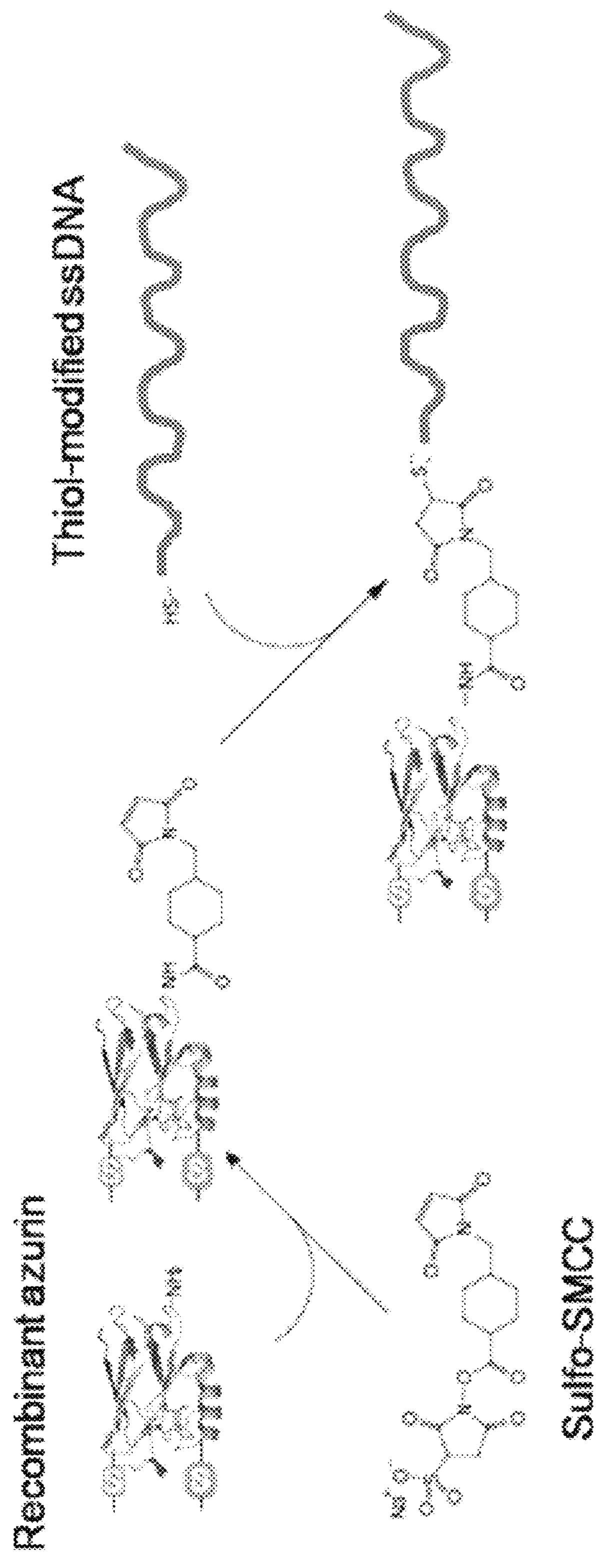
FIGS. 1*a* to 1*d* are diagrams showing four methods of preparing a recombinant azurin-SMCC-DNA hybrid.
Figure 1B:
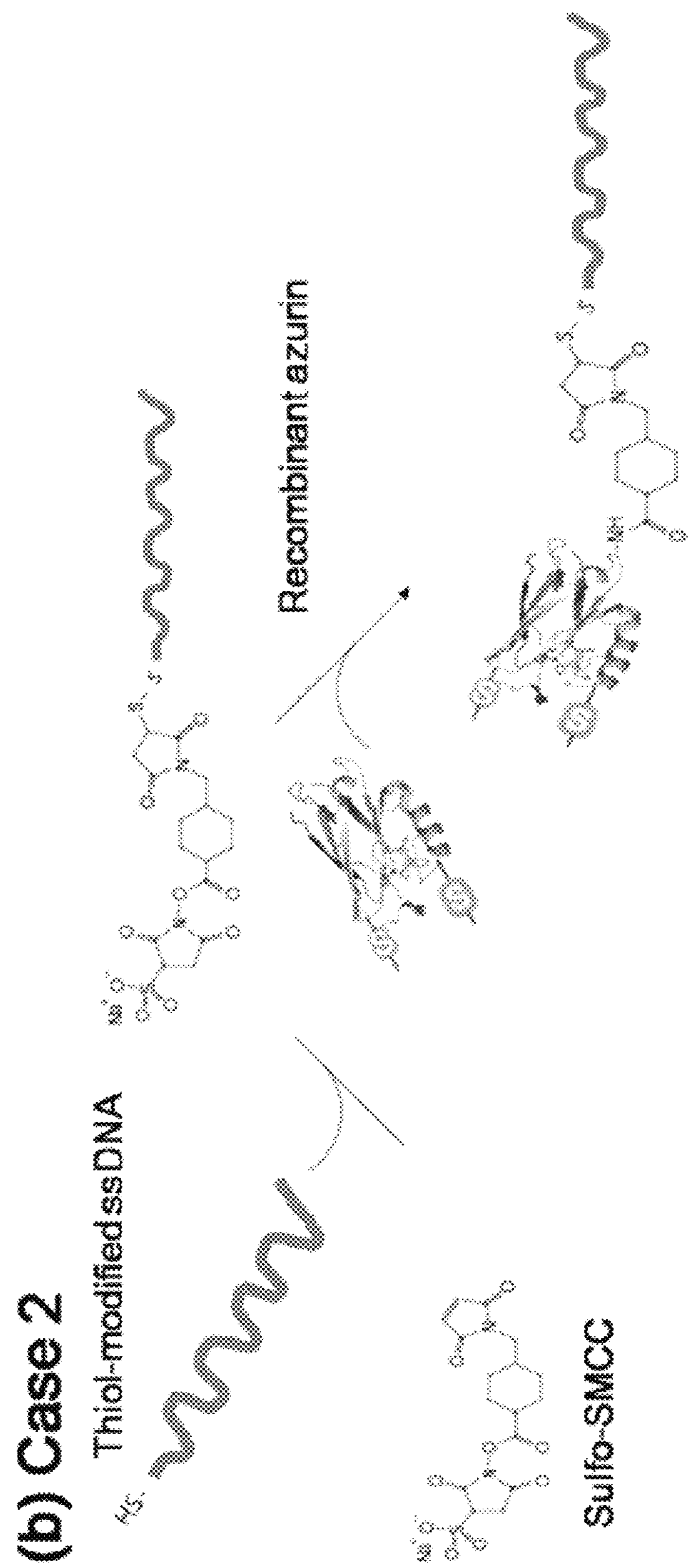
Figure 1C:
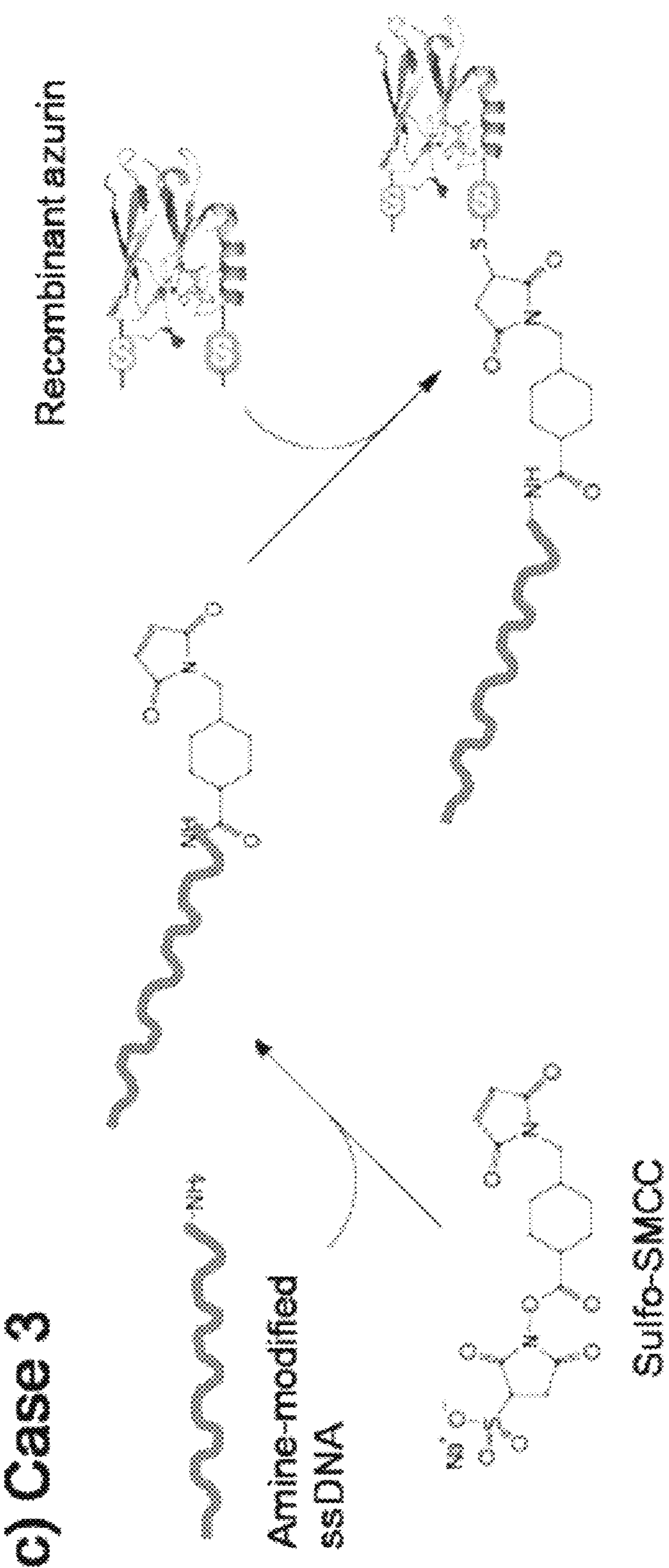
Figure 1D:
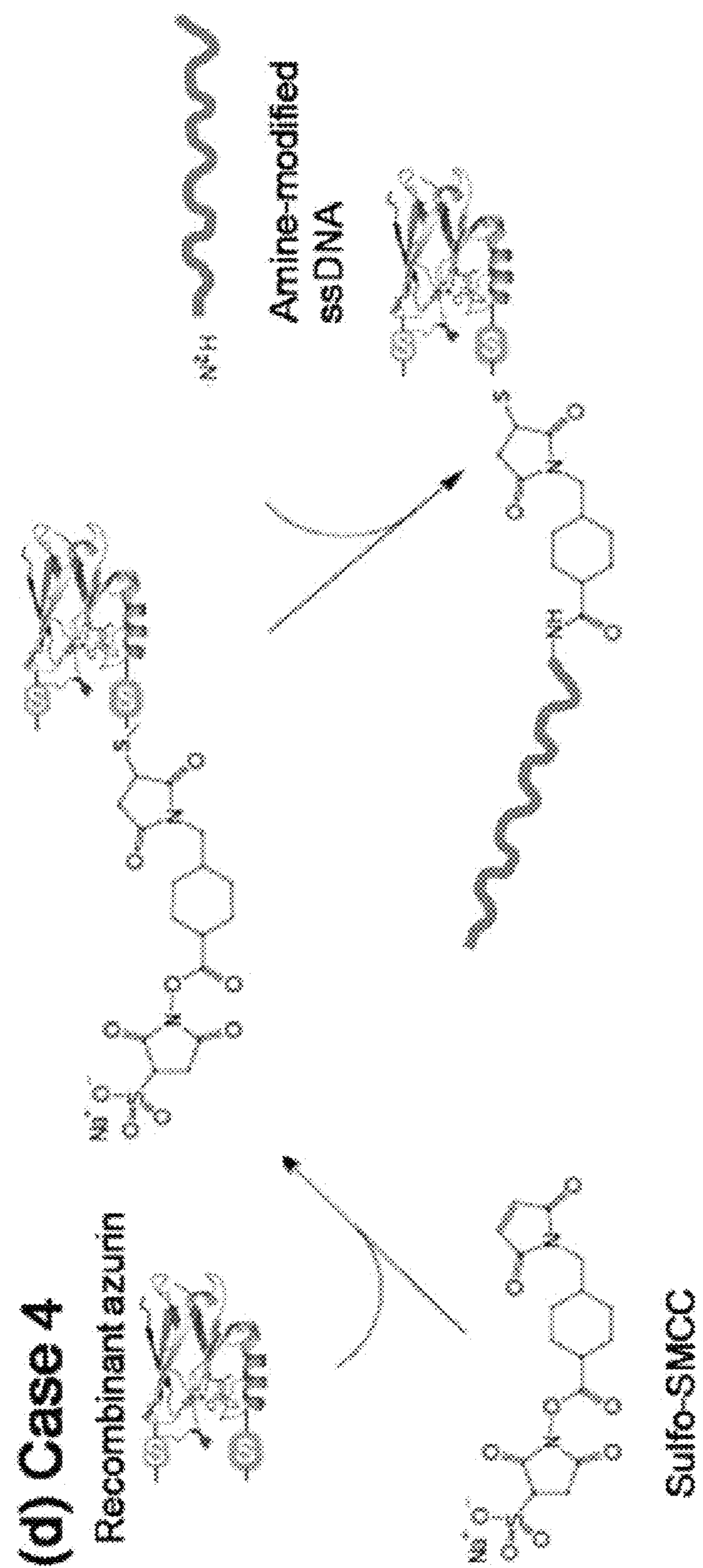

Hereinafter, the present invention will be described in detail with reference to examples. These examples are only for illustrating the present invention more specifically, and it will be apparent to those skilled in the art that the scope of the present invention is not limited by these examples.

EXAMPLES

1. MATERIALS AND METHODS 1.1. Materials

The cysteine-modified azurin was expressed and purified as described previously (H. Song et al., 2011). The single strand DNA (5' CCCGGGAAAACCCGGGTTTTC-CCGGGAAAACCCGGG TTTTCCCGAAAAAAAA-3'; SEQ ID NO:1) was modified with a thiol-group on the 5 prime end for proper conjugation between recombinant azurin and ssDNA via sulfo-SMCC by CLM. The complementary ssDNA (5'-AACCAACCTTTTTTTT-3'; SEQ ID NO:2) was prepared and it was modified with a thiol group at the 5 prime end (thiol-modified complementary-ssDNA: thiol-cDNA) for conjugation to the conducting nano particles and biotinylated cDNA (5'-AACCAACCTTTTTTTT-3'; SEQ ID NO:2) was prepared for streptavidin coated CdSe—ZnS. All modified ssDNAs were supplied by Bioneer (Korea). The gold nanoparticles (GNP, 10 nm size) were purchased from BBI international (UK). The streptavidin-coated quantum dot (CdSe—ZnS, 625 nm) was purchased from Invitrogen (USA). The Sulfosuccinimidyl-4-(N-maleimidomethyl) cyclohexane-1-carboxylate (Sulfo-SMCC) and the dithiothreitol (DTT), Ellman's reagent were purchased from Pierce (USA). The copper(II) sulfate (Cu2SO4), cobalt(II) chloride (CoCl2), manganese (II) sulfate monohydrate (MnSO4.H2O), Iron (III) Oxide (Fe2O3), nickel chloride (NiCl2), zinc sulfate (ZnSO4), ethyl acetate, (4-(2-hydroxyethyl)-1-piperazineethanesulfonic acid) (HEPES), N,N-Dimethylformamide (DMF) were purchased from Sigma Aldrich Co (USA). Distilled and deionized (DI) water was used to clean the substrates.

As a working electrode, Au substrates (Au (200 nm)/Cr (2 nm)/SiO2 wafers) were purchased from G-mek (Korea) and used in the Raman spectroscopy, AFM and electrochemical experiments. The Pt counter electrode and Ag/AgCl reference electrode were purchased from BAS (USA).

1.2. Genetic Engineering of *Pseudomonas Aeruginosa* Azurin

An *Escherichia coli* strain DH5a was used as the host for subcloning. Standard techniques were employed throughout this work. The gene encoding blue copper protein azurin was amplified using polymerase chain reaction (PCR) from the genomic DNA of *Pseudomonas aeruginosa*. The forward primer was designed to contain a NcoI restriction enzyme site and the reverse primer was designed to contain a BamHI restriction enzyme site The PCR product was purified using a DNA purification kit (QIAZEN, USA) and digested with two restriction enzymes for NcoI and BamHI (New England Biolabs, UK). The digested DNA fragments were ligated with a pET-21a(+) vector (Novagen, Germany), which was predigested with NcoI and BamHI, using a ligation kit (TaKaRa, Japan). Azu Cys F and Azu Cys R primers were designed to contain a mutant site for site-directed mutagenesis (SDM) and used to change the codon for Lys92Cys (K92C) from AAG to TGC. Mutations in the azu gene were introduced using the SDM.

1.3. Expression and Purification of Recombinant Azurin Variants

The plasmids, containing genes for azurins, were transformed into *E. coli* BL21 (DE3). 20 The transformants were grown to an OD of 0.6 at 37° C. in shake flasks containing 1 L of LuriaeBertani medium (0.5% yeast extract, 1.0% tryptophan, and 1.0% NaCl) with 50 mg/mL ampicillin. Expression was induced by adding isopropyl b-D-thiogalactopyranoside (IPTG) to a final concentration of 0.839 mM. The transformed cells were grown for an additional 16 h at 37° C. The cells were harvested by centrifugation at 5000 g for 15 min at 4° C. The cell paste was resuspended in sucrose buffer (20% sucrose, 0.3 M TriseHCl, pH 8.1, 1 mM EDTA) and subjected to osmotic shock (0.5 mM MgCl2). Contaminating proteins were precipitated from the periplasmic preparation by decreasing the pH to 3.8 (50 mM sodium acetate), yielding azurin-containing supernatant. Apo-azurin and cysteine-modified apo-azurin fractions (Elution pH 4.6 and 4.8, respectively) were separated on a CM excellulose ion-exchange column with a pH gradient from 4.0 to 6.0 (50 mM sodium acetate).

1.4. Fabrication of Recombinant Azurin-SMCC-DNA Conjugates

To obtain the high-yield of the recombinant azurin-SMCC-DNA conjugates, we tried 4 types of conjugation methods with different steps and strategies. FIG. 1 depicted these procedures.

(1) The recombinant azurin of amine group was reacted with sulfo-SMCC to form amide bond, and then, thiol-modified ssDNA (sulfhydryl-containing biomolecule) is added to react with the maleimide group with recombinant azurin-sulfo SMCC for forming stable thioether bond. As a result, the recombinant azurin-SMCC-DNA conjugate was prepared.

50 μM×100 μl of the recombinant azurin was mixed with the 100 μM×200 μl of Sulfo-SMCC. Prepared samples mixed for conjugation during 6 hrs at room temperature with shaker. And then, the sulfo-SMCC tagged recombinant azurin was purified and the unreacted the recombinant was removed by ultrafiltration with MWCO 3k Amicon Ultra centrifugal filter (Millipore, USA). While making the sulfo-SMCC tagged recombinant azurin, 50 μM of thiol-modified ssDNA of 100 μl was prepared. For the thiol-modified ssDNA activation, thiol-modified ssDNA was further reduced by 20 mM DTT for 30 min at room temperature to obtain free sulfhydryl groups. And then, 100 μl of ethyl acetate added to DNA solution, for removing saturated DTT. The reduced thiol-modified ssDNA was transferred to the conjugation buffer (20 mM Tris, 50 mM NaCl, and 1 mM EDTA pH 7.0) by using a desalting column (PD-10). And then, thiol-activated ssDNA was reacted with maleimido-activated sulfo-SMCC tagged recombinant azurin, followed by 3 hrs incubation at room temperature in shaker. And then, the sulfo-SMCC tagged ssDNA was purified and the unreacted DNA, the recombinant azurin was removed by ultrafiltration with MWCO 3k Amicon Ultra centrifugal filter (Millipore, USA). The resulting recombinant azurin-SMCC-DNA was further purified by S excellose ion-exchange column (Bioworks, Sweden) with a continuous sodium chloride gradient from 0 to 1 M.

(2) The thiol-modified ssDNA (sulfhydryl-containing biomolecule) is reacted with sulfo-SMCC. And then, the recombinant azurin was added to thiol-modified ssDNA-sulfo SMCC for form amide bond. As a result, the recombinant azurin-SMCC-DNA conjugate was prepared.

50 μM of thiol-modified ssDNA (52 mer) of 100 μl which diluted in HEPES buffer (pH 7.0) was prepared. For the thiol-modified ssDNA activation, thiol-modified ssDNA was further reduced by 20 mM DTT for 30 min at room temperature to obtain free sulfhydryl groups. And then, 100 μl of ethyl acetate added to DNA solution, for removing saturated DTT. The reduced thiol-modified ssDNA was transferred to the conjugation buffer (20 mM Tris, 50 mM NaCl, and 1 mM EDTA pH 7.0) by using a desalting column (PD-10). While making free SH-DNA, The 100 μM of Sulfo-SMCC 200 μl in DMF was prepared. Prepared samples mixed for conjugation during 6 hrs at room temperature with shaker. And then, the sulfo-SMCC tagged ssDNA was purified and the unreacted DNA was removed by ultrafiltration with MWCO 3k Amicon Ultra centrifugal filter (Millipore, USA). The same molar ratio of recombinant azurin was reacted with maleimido-activated sulfo-SMCC tagged ssDNA, followed by 3 hrs incubation at room temperature in shaker. The resulting recombinant azurin-SMCC-DNA was further purified by S excellose ion-exchange column (Bioworks, Sweden) with a continuous sodium chloride gradient from 0 to 1 M. Purified protein was dialyzed against a HEPES buffer. The collected recombinant azurin-SMCC-DNA was concentrated by repeated ultrafiltration (MWCO 3k Amicon Ultra centrifugal filter).

(3) The amine-modified DNA was reacted with sulfo-SMCC to form amide bond. And then, the recombinant azurin was treated with DTT for reducing cysteine group of azurin molecule. And then, the recombinant azurin was reacted with amine-modified DNA-sulfo SMCC to form thioether bond. So, the recombinant azurin-SMCC-DNA conjugate was prepared.

50 μM of amine-modified ssDNA (52 mer) of 100 μl which diluted in HEPES buffer (pH 7.0) was reacted with the 100 μM of sulfo-SMCC 200 ul in DMF for 6 hrs in shaker. Then, for the thiol group-reduction of cyestine-modified azurin, the recombinant azurin was further reduced by 20 mM DTT for 30 min at room temperature to obtain free sulfhydryl groups. And then, 100 μl of ethyl acetate added to protein solution, for removing saturated DTT. The reduced thiol-reduced recombinant azurin was transferred to the conjugation buffer (20 mM Tris, 50 mM NaCl, and 1 mM EDTA pH 7.0) by using a desalting column (PD-10). Then, the recombinant azurin-sulfo SMCC was purified and the unreacted sulfo SMCC was removed by ultrafiltration with MWCO 3k Amicon Ultra centrifugal filter (Millipore, USA). The same molar ratio of recombinant azurin was reacted with maleimido-activated ssDNA-sulfo SMCC to form amide bond. This step was followed by 3 hrs incubation at room temperature in shaker. The resulting recombinant azurin-SMCC-DNA was further purified by S excellose ion-exchange column (Bioworks, Sweden) with a continuous sodium chloride gradient from 0 to 1 M. Purified protein was dialyzed against a HEPES buffer. The collected recombinant azurin-SMCC-DNA was concentrated by repeated ultrafiltration (MWCO 3k Amicon Ultra centrifugal filter).

(4) The recombinant azurin was treated with DTT for reducing cysteine group of azurin molecule. And, the thiol-activated azurin was reacted with sulfo-SMCC to form thioether bond. Then, the amine-modified DNA was added to the recombinant azurin-sulfo SMCC molecules.

To obtain free sulfhydryl group of recombinant azurin, the recombinant azurin was further reduced by 20 mM DTT for 30 min at room temperature to obtain free sulfhydryl groups. And then, 100 μl of ethyl acetate added to protein solution, for removing saturated DTT. The reduced thiol-reduced recombinant azurin was transferred to the conjugation buffer (20 mM Tris, 50 mM NaCl, and 1 mM EDTA pH 7.0) by using a desalting column (PD-10). The prepared recombinant azurin was reacted with reacted with the 100 μM of sulfo-SMCC 200 ul in DMF for 6 hrs in shaker. The recombinant azurin-sulfo SMCC was purified and the unreacted SMCC was removed by ultrafiltration with MWCO 3k Amicon Ultra centrifugal filter (Millipore, USA). In addition, 50 μM of amine-modified ssDNA (52 mer) of 100 μl was added to the recombinant azurin-sulfo SMCC for forming amide bond by NHS esters reacting with primary amine for 3 hrs in shaker. The resulting recombinant azurin-SMCC-DNA was further purified by S excellose ion-exchange column (Bioworks, Sweden) with a continuous sodium chloride gradient from 0 to 1 M. Purified conjugate was dialyzed against a HEPES buffer. The collected recombinant azurin-SMCC-DNA (recombinant azurin/DNA hybrid) was concentrated by repeated ultrafiltration (MWCO 3k Amicon Ultra centrifugal filter).

In conclusion, (2) method is best method to obtain high-yield of the recombinant azurin-SMCC-DNA conjugates.

The detailed description should be followed. Also, the cDNA/nanoparticle hybrid was followed by previous study (S. J. Hurst et. al., 2006).

1.5. Fabrication of the Recombinant Azurin/DNA Hybrid Layer

To fabricate the bioprocessing device as a working electrode, an Au working electrode was prepared on $Si/SiO_2$ substrates on the bulk scale. The fabricated Au electrode was cleaned in a piranha solution, which consisted of 30 vol % $H_2O_2$ (Daejung Chemical Co. Ltd., Korea) and 70 vol % $H_2SO_4$ (Daejung Chemical Co. Ltd., Korea) at 70° C. for 3 min. The Au electrode was then rinsed with deionized water and dried using a stream of nitrogen.

With these prepared Au substrates, 30 μM of a recombinant azurin-SMCC-DNA solution was dropped onto the Au substrate for direct self-assembly on the Au surface via the cysteine group of the recombinant azurin. After 6 hrs, an immobilized recombinant azurin-SMCC-DNA layer formed on the Au surface. To remove excess recombinant azurin-SMCC-DNA molecules, the modified electrode was thoroughly rinsed with deionized water and dried using nitrogen gas. To modulate the electrochemical signal, (1) 30 μM of complementary-ssDNA (cDNA) was immobilized onto the self-assembled recombinant azurin/DNA hybrid layer for 6 hrs. (2) Also, the thiol-modified complementary-ssDNA (thiol-cDNA)/gold nanoparticle and thiol-cDNA2/silver nanoparticle hybrids were prepared.

To prepare the thiol-cDNA/nanoparticle hybrids, 30 μM of thiol-modified cDNA was reduced with 20 mM DTT for 30 min at room temperature, which produced the free sulfhydryl groups for the thiol-modified ssDNA activation. 100 μl of ethyl acetate was then added to the DNA solution to remove saturated DTT. The reduced thiol-modified ssDNA was transferred to 10 mM HEPES buffer using a desalting column (PD-10). The reduced thiol-modified ssDNA was then mixed with 300 μl gold or silver colloids and the mixture was shaken for 6 hrs at room temperature. The mixed solution was centrifuged at 4000 rpm for 40 min three times. The precipitate was redispersed into 300 μl of the HEPES buffer and stored at 4° C.

These cDNA/nanoparticle hybrids were dropped onto the self-assembled recombinant azurin/DNA hybrid layer for 6 hrs. (3) For immobilization of the heavy metal ions, the self-assembled recombinant azurin/DNA hybrid was dipped into heavy metal ions solutions, including copper (II) sulfate ($Cu_2SO_4$), cobalt(II) chloride ($CoCl_2$), manganese (II) sulfate monohydrate ($MnSO_4.H_2O$), iron (III) oxide ($Fe_2O_3$), nickel chloride ($NiCl_2$) and zinc sulfate ($ZnSO_4$), for 6 hrs. To remove excess modulating materials, the modified electrode was then thoroughly rinsed with deionized water and dried using nitrogen gas.

1.6. The Morphology Analysis of Recombinant Azurin/DNA Hybrid Layer

Figure 2A:
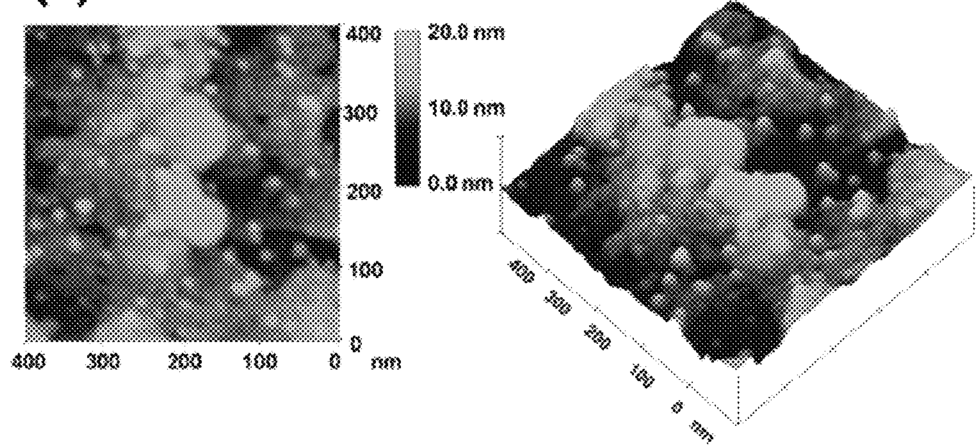
FIGS. 2*a* to 2*c* are images confirming topographies of a recombinant azurin (FIG. 2*a*), a thiol-modified ssDNA (FIG. 2*b*), and a recombinant azurin/DNA hybrid (FIG. 2*c*), immobilized onto a gold substrate surface, by using an atomic force microscope.
Figure 2B:
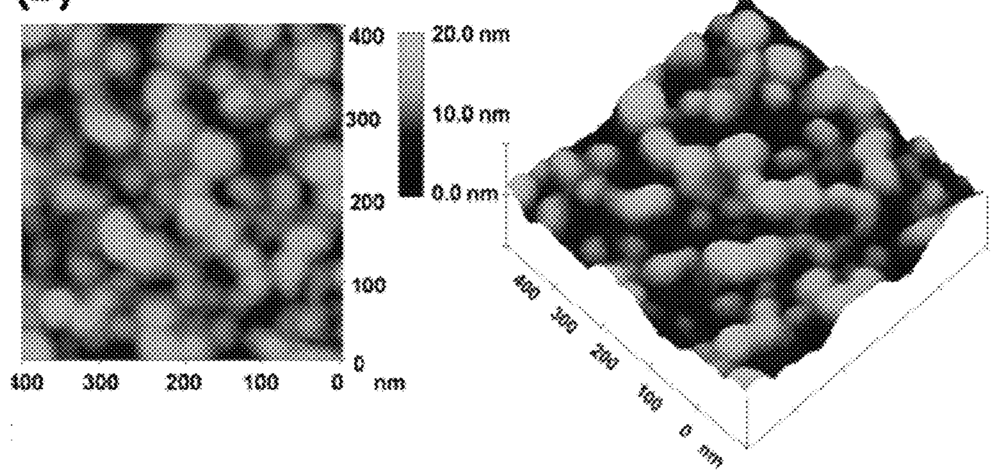
Figure 2C:
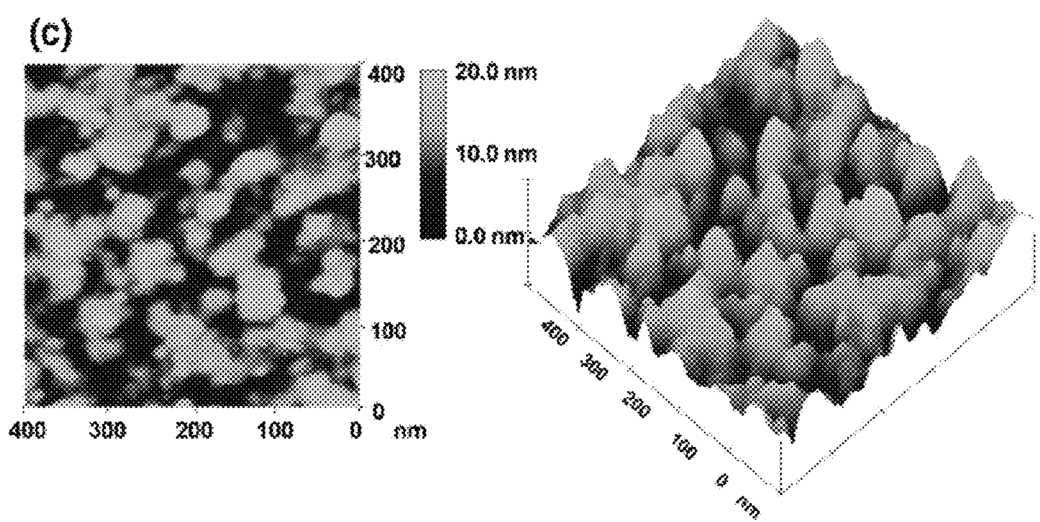

The prepared recombinant azurin/DNA hybrid was self-assembled on an Au substrate. The modified surfaces were then investigated by AFM to verify successful immobilization of the recombinant azurin/DNA hybrid on the Au electrodes. FIG. 2*a* shows the topography of the immobilized thiol-modified ssDNA layer, which formed 20-30 nm lumps. FIG. 2*b* depicts the recombinant azurin layer, which contained cysteine residues for direct immobilization. Consequently, the cysteine-modified azurin appeared as small lumps, which ranged in size from 30-40. These results indicate that the cysteine-modified proteins had self-assembled with good orientation, presumably, due to the link between the thiol-group and Au surface. Moreover, FIG. 2*c* clearly shows the self-assembled recombinant azurin/DNA hybrid layer, where the molecular size of the clusters ranged from 10-40 nm. This topology was clearly distinct from the topology shown in FIG. 2*c*. These results demonstrate that there was a clear distinction regarding thiol-modified ssDNA, recombinant azurin and recombinant azurin/DNA hybrid layers. Thus, the recombinant azurin/DNA hybrids were well ordered and formed on the Au substrate.

The surface topography of the fabricated recombinant azurin/DNA hybrid layer was investigated by AFM (Digital instruments Nanoscope® IV, USA) at room temperature. The AFM was equipped with a 1-10 Ω-cm Phosphorous (n) doped (Si) tips (RTESP tip), which had a resonant frequency between 230-305 kHz. The size of all images was 500 nm×500 nm and a scan rate of 1.0 Hz was used.

1.7. The Biofilm Composition Analysis of Recombinant Azurin/DNA Hybrid

To confirm the surface characteristics and morphologies of recombinant azurin/DNA hybrid, Raman spectroscopy was used. (FIG. 3*e*, left) shows the Raman spectra of blue copper azurin (600-1750 $cm^{-1}$). The Raman spectra contained a Raman peak between 200-300 $cm^{-1}$, which was related to $Cu^{2+}$—S (cys) stretch, a peak centered around 400 $cm^{-1}$ with overtones, which corresponds to the RS—→$Cu^{2+}$ bond and a C—S(cys) stretch peak at 800 $cm^{-1}$. These results are in a good agreement with previous reports.

The Raman spectrum of ss-DNA between 600-1750 $cm^{-1}$ (FIG. 3*e*, middle) contained various Raman peaks, which reflected the different components and structure of the ssDNA. The nucleosides can be identified by bands that are characteristic of the different kinds of nucleotide (A, G, T and C) markers, where the interval between 620-680 $cm^{-1}$ corresponds to guanine nucleoside, the band near 727 $cm^{-1}$ identifies the adenine residue, and the thymidine marker near 770 $cm^{-1}$ identifies C2'-endolanti conformers of dT. In addition, the bands between 800-1100 $cm^{-1}$ are sensitive to the backbone geometry and secondary structure, where the "B-form" has a peak near 838 $cm^{-1}$. The PO2-peak occurs at 1092 $cm^{-1}$. Also, various bands in the 1200-1750 $cm^{-1}$ region have been assigned to purine and pyrimidine ring vibrations. The band near 1219 $cm^{-1}$ is due predominantly to dT, while the band near 1256 $cm^{-1}$ has been assigned to dC. The most informative of these bands are the bands corresponding to guanine at 1489 $cm^{-1}$. The broad band centered near 1668 $cm^{-1}$, assigned to coupled C═O stretching and N—H deformation modes of dT, dG, and dC. The observed Raman peaks of ss-DNA and their assignments were listed in Table. 1.

TABLE 1

| Raman Shift (cm−1) | Assignment |
|---|---|
| 630 | dC |
| 680 | dG |
| 730 | Da |
| 781 | dT, dC, bk |
| 830 | vOPO |
| 890 | D |
| 1019 | dT, dG, dC |
| 1092 | $vPO^{2-}$ |
| 1160 | dG |
| 1219 | dC, dT |
| 1256 | dA, dC |
| 1331 | dA, dG |
| 1485 | dA, dG |
| 1573 | dA, dG |
| 1668 | dT |

Figure 3A:
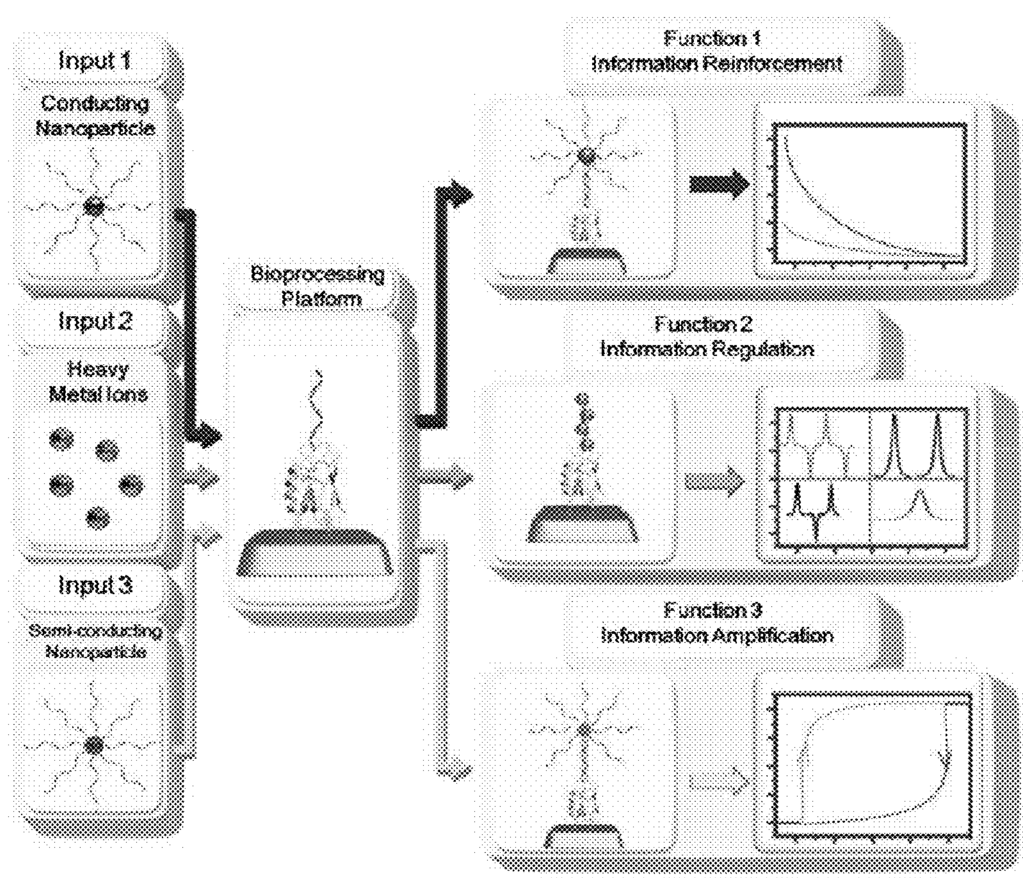
FIGS. 3*a* to 3*e* are images showing characteristics of a recombinant azurin/DNA hybrid.
Figure 3B:
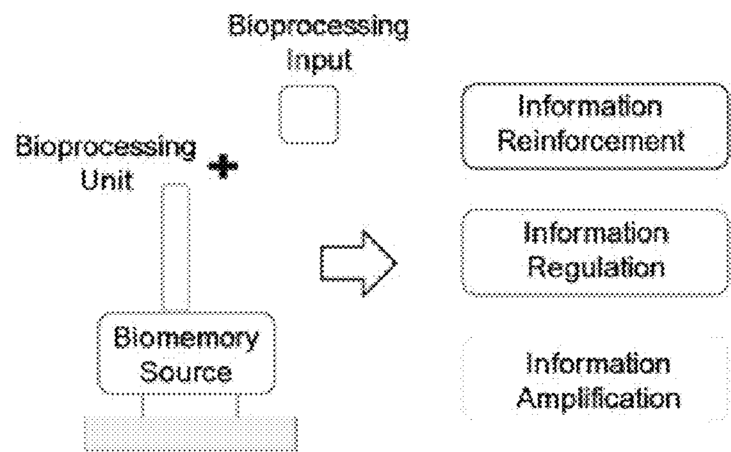
Figure 3C:
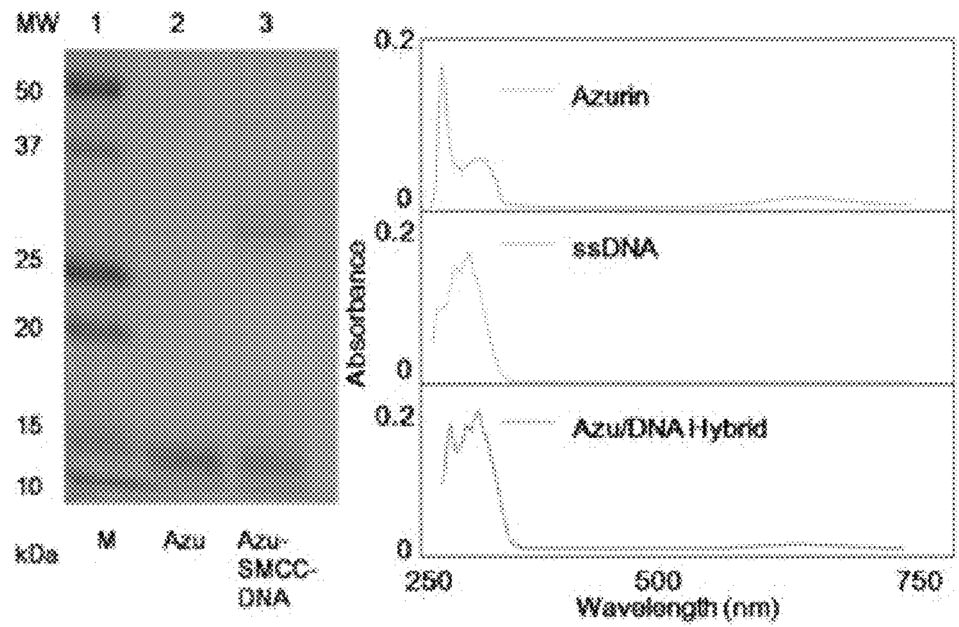
Figure 3D:
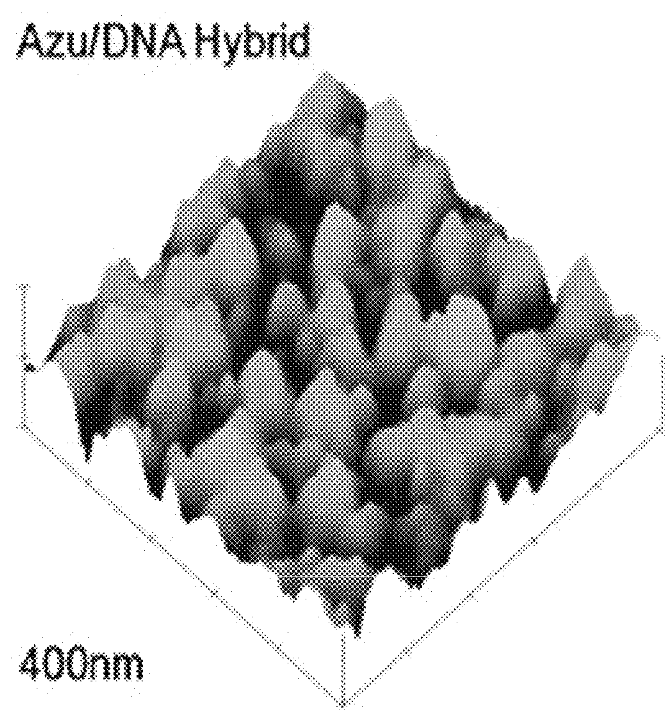
Figure 3E:
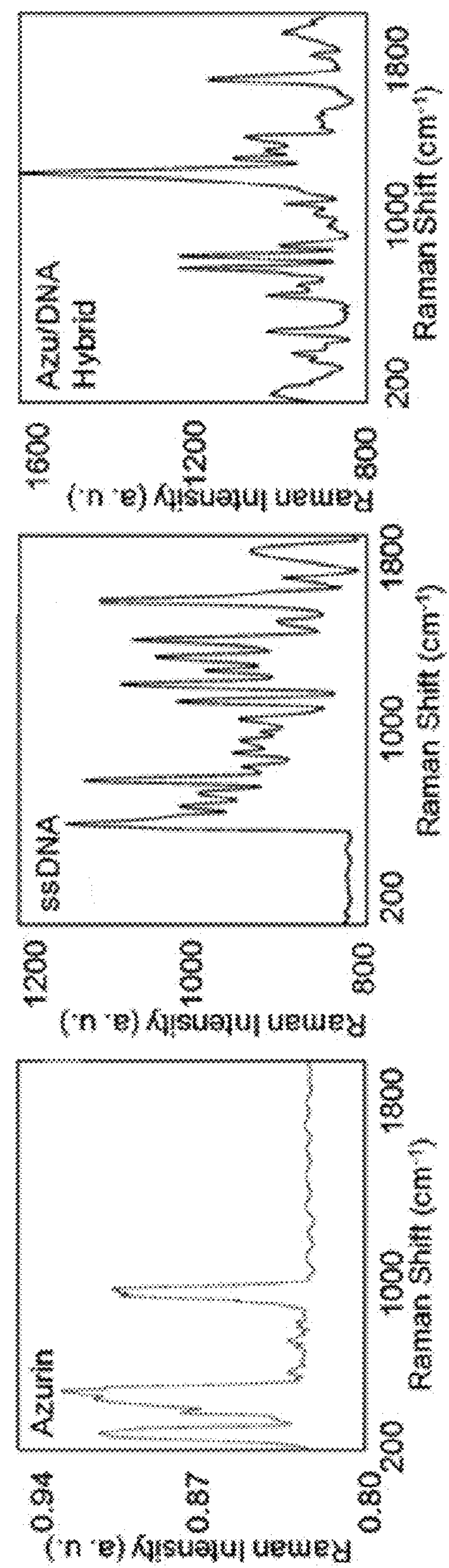

The recombinant azurin does not absorb in the spectral region from 900 $cm^{-1}$ to 1750 $cm^{-1}$ (FIG. 3*e*, left), while the DNA spectrum was rich with peaks within this Raman range (900 $cm^{-1}$ to 1750 $cm^{-1}$). This difference allowed us to identify the conjugation between azurin and the ssDNA. The interaction between the recombinant azurin and ss-DNA was investigated based on a comparison the Raman spectrum of ssDNA with the spectrum of recombinant azurin and the spectrum from ssDNA under identical conditions. (FIG. 3*e*, right) shows the Raman spectra of the recombinant azurin/DNA hybrid, which contained the following peaks due to the ssDNA and the recombinant azurin interaction: (1) the appearance of a Raman band in the range from 200 $cm^{-1}$ to 600 $cm^{-1}$ was related to the presence of the recombinant azurin, which appeared in the region between 200-300 $cm^{-1}$ ($Cu^{2+}$—S (cys) stretch) and at around 400 $cm^{-1}$ ($RS^{-} \rightarrow Cu^{2+}$ bond). (2) The Raman peak of the recombinant azurin was related to the C—S(cys) stretch (800 $cm^{-1}$) overlapped with the Raman peak from DNA at 781 $cm^{-1}$ (dT, dC, bk). (3) The band at 1485 $cm^{-1}$ in the Raman DNA spectrum (FIG. 3*e*, table) corresponded to the δC8H and N9C8-C8-N7 guanine vibration. This band was found to be upshift (1490 $cm^{-1}$) due to the interaction between the recombinant azurin and ssDNA (FIG. 3*e*, right). Thus, the interaction of DNA with the recombinant azurin in the region of the G-C pairs occurs at the N7 site of the guanine or with the external side of the imidazole moiety of the guanine. (4) Moreover, this interaction caused an increase in the intensity and upshift of the band at 1573 $cm^{-1}$, which was attributed to the adenine C5C4-C4N3 internal vibrations and guanine C4N3-05C4-N7C5 internal vibrations. The intensity and position variation of this band during the interaction were mainly caused by the interaction between the recombinant azurin and guanine at the N7 position of guanine. Thus, the recombinant azurin interacts with the N7 positions of adenine and guanine and this interaction leads a partial deformation of the hydrogen bonds between adenine and thymine bases. (5) On the other hand, the interaction between ssDNA and the recombinant azurin decreased the peak intensity at 1668 $cm^{-1}$ (FIG. 3*e*, right). This band corresponded to thymine, which contributes to the C5C4 and C40 vibrations of the thymine groups. This decrease could be due to a shift to a lower frequency of the C═O stretching and N—H deformation modes. Thus, the interaction of the recombinant azurin in this position could change the DNA structure via deformation of the hydrogen bond between the NH2 group of the adenine and the C40 group of the thymine molecule. (6) Moreover the intensity of the Raman bands at 1219 and 1257 cm-1, which are highly hypochromic in B-DNA decreased, which indicted that there was an interaction between the recombinant azurin or ssDNA at the N—H sites of dT and dC. All peaks values are listed in Table 1. In conclusion, the fabricated recombinant azurin/DNA hybrid layer was shown to be immobilized and oriented on the Au surface and could be used as a biomemory modulator.

The Raman spectrum was monitored using a Scanning Confocal Raman Spectrometer (NTMDT, Russia), which was equipped with an inverted optical microscope (Olympus IX71, Japan). The raman spectra were obtained from an near infrared laser, which emitted light at a wavelength of 785 nm. The scanning range was 200-1750 cm-1 and the mean intensity was used as the Raman signals. The scanning range was up to 100 μm×100 μm×6 μm (X, Y, Z axis) and scanning time was 10 s. The maximum resolution in the XY plane was 200 nm and 500 nm.

1.8. The Electrochemical Properties I

Figure 4:
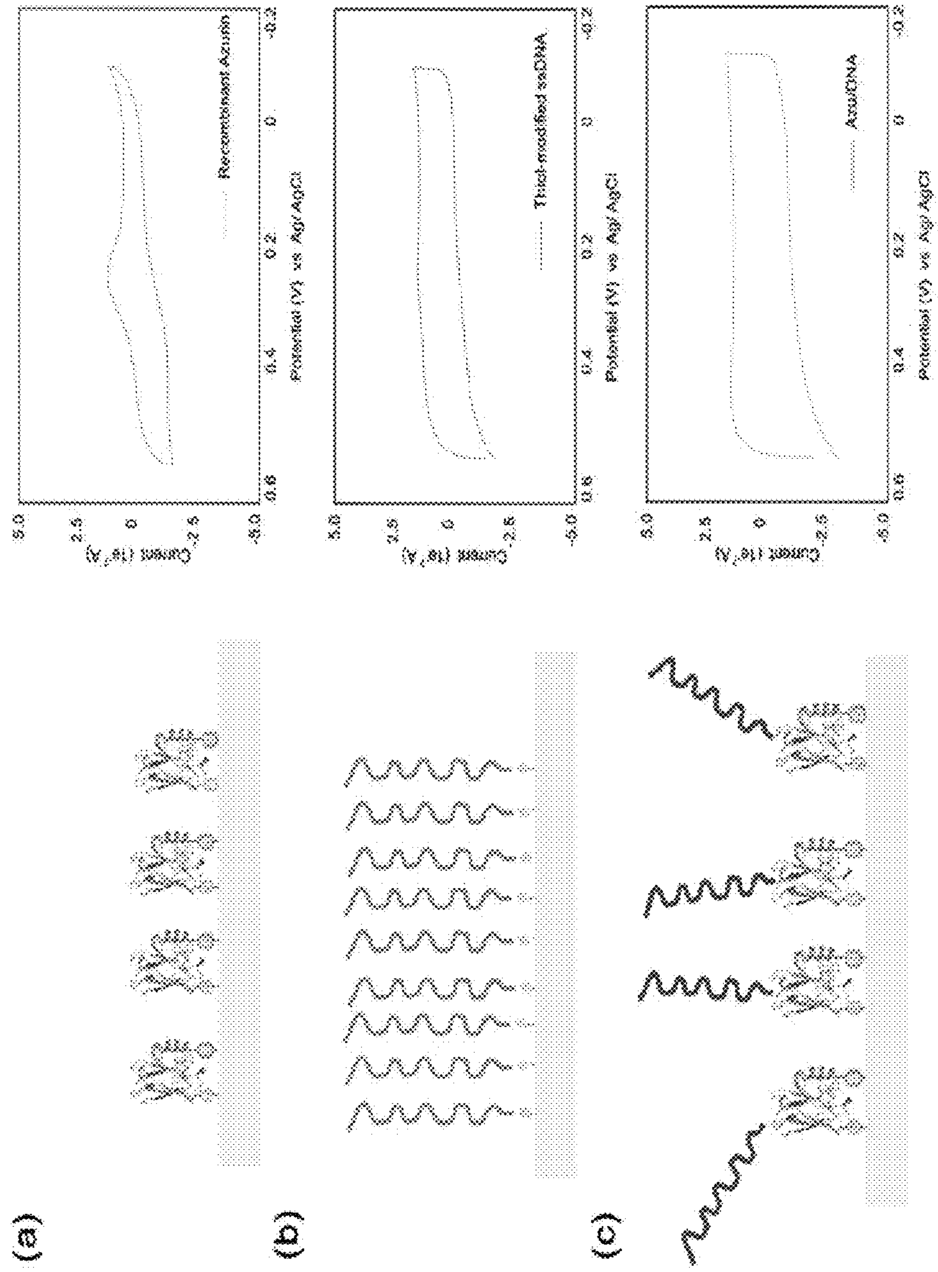
FIGS. 4*a* to 4*c* show schematic diagrams and cyclic voltammetry results of a recombinant azurin (FIG. 4*a*), a thiol-modified ssDNA (FIG. 4*b*), and a recombinant azurin/DNA hybrid (FIG. 4*c*), immobilized onto a gold substrate surface.

In this study, each part of the bioconjugate was designed to align their particular role. The recombinant azurin was immobilized on the Au substrate through a cysteine-residue, which functioned as the platform module. A hetero bifunctional linker sulfo-SMCC was used to connect the recombinant azurin and the thiol-modified DNA molecule. The thiol-modified ssDNA functioned as a signal receptor module when the input signal operator material was added. To compare the redox property of the recombinant azurin, ssDNA, recombinant azurin/DNA hybrid, we initially measured the cyclic voltammetry (CV). Each sample was repeated 5 times, respectively (FIG. 4). In the case of recombinant azurin, redox properties were observed and its reduction potential and oxidation potential were 159±23 mV and 272±22 mV, respectively. The reduction potential and oxidation potential of the thiol-modified ssDNA were 93±19 mV and 292±26 mV, respectively. In case of the recombinant azurin/DNA hybrid, its redox and oxidation potential values were 187±31 mV and 301±14 mV, respectively. The reduction potential value was similar to that of recombinant azurin and the oxidation potential value was similar to that of ssDNA. Presumably, the redox potentials originated from the recombinant azurin. Both peaks were visible and coincident with normal azurin. The reduction current of the recombinant azurin, ssDNA, recombinant azurin/DNA hybrid was 1.783±0.281 μA, 1.264±0.377 μA, 1.888±0.394 μA, respectively. In addition, the values for the recombinant azurin, ssDNA, recombinant azurin/DNA hybrid were −2.124±0.455 μA, −1.761±0.263 μA, −1.645±0.123 μA, respectively. Each value was listed in table 2. These results clearly indicate that the redox properties of recombinant azurin/DNA hybrid were altered by conjugation. The natural properties of biomolecule and electron transfer kinetics can change the redox properties of a conjugate compound. Based on these results, we concluded that the recombinant azurin/DNA hybrid self-assembled on Au working electrode and displayed the appropriate electrochemical properties. Further experiments will be conducted to assess the biomemory modulating performance of this device.

1.9. The Basic Mechanism of Information Regulation

The proposed biomemory modulating device was operated using electrochemical methods. Presumably, the basic principle of signal regulation was elucidated by electron transfer at the biomolecule-input molecule interface and its energy level perturbation of the donor-bridge-acceptor system. In case of recombinant azurin-SMCC-DNA conjugate, the perturbed energy levels will exist in vicinity of the energy levels of Azurin and ssDNA. But, when input materials were added to recombinant azurin-SMCC-DNA conjugate, the bridge was provided to facilitate the electron transfer at the DNA-Metal ions interfaces. Furthermore, the heterogeneous electron transfer is influenced by several factors such as environmental conditions (structure/orientation, size of ions), diffusion rate, injection rate. The input materials were strongly provided the bridge between donor and acceptor system which will overcome the energy levels between donor and acceptor. The following cell reaction describes the basic mechanism of signal regulation.

Au/Recombinant azurin/SMCC/DNA/−HEPES−H+/Pt (1)

Au/Recombinant azurin/SMCC/DNA/cDNA/Metal ions/−HEPES−H+/Pt (2)

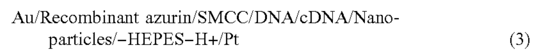

Au/Recombinant azurin/SMCC/DNA/cDNA/Nanoparticles/−HEPES−H+/Pt (3)

Compared to reaction (1), reaction (2), and reaction (3) exists the bridge. It is likely that the various input materials such as metal ions and nanoparticle adjust those energy levels. This phenomenon enables to electrochemical signal regulation.

1.10. The Electrochemical Properties II

Figure 5:
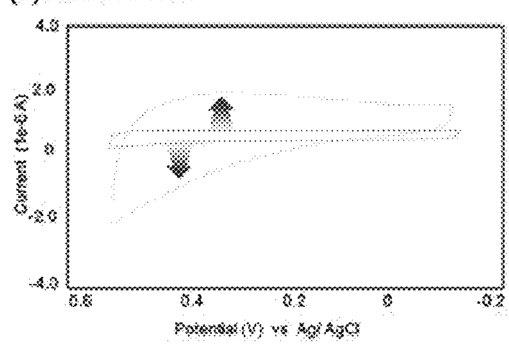
FIGS. 5*a* to 5*f* show cyclic voltammetry results of a recombinant azurin/DNA hybrid/Mn ion (FIG. 5*a*), a recombinant azurin/DNA hybrid/Fe ion (FIG. 5*b*), a recombinant azurin/DNA hybrid/Co ion (FIG. 5*c*), a recombinant azurin/DNA hybrid/Zn ion (FIG. 5*d*), a recombinant azurin/DNA hybrid/Ni ion (FIG. 5*e*), and a recombinant azurin/DNA hybrid/Cu ion (FIG. 5*f*).
Figure 5:
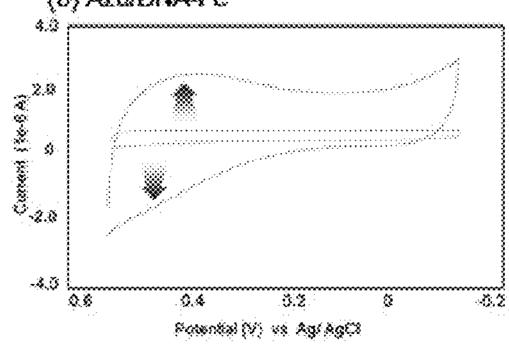
Figure 5:
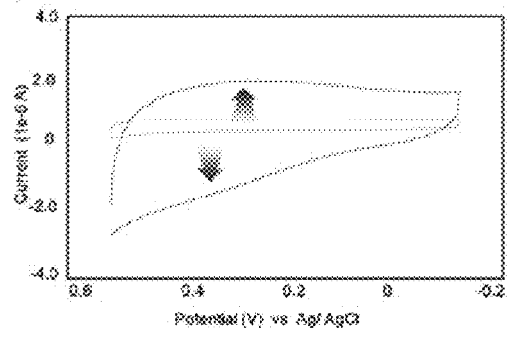
Figure 5:
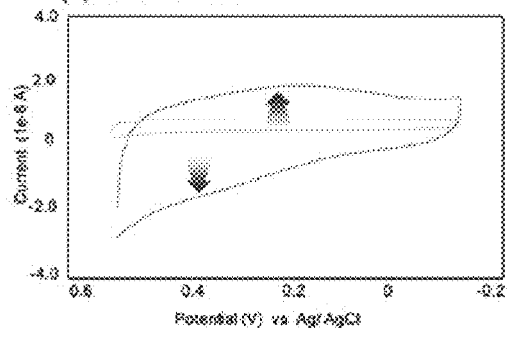
Figure 5:
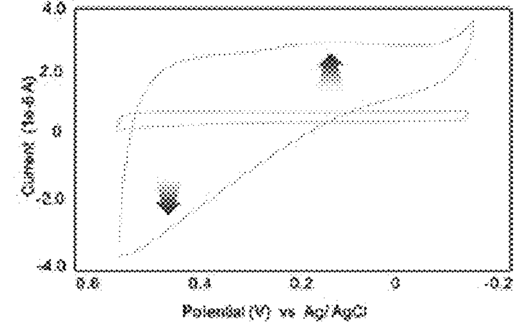
Figure 5:
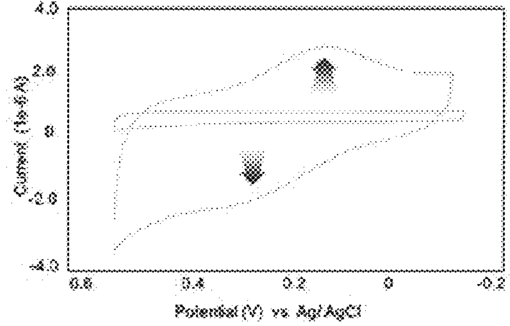

When various heavy metal ions were added to the recombinant azurin/DNA hybrid, the cyclic voltamogram of each case of redox potentials specified are in FIG. 5. The reduction and oxidation potentials of the Mn ions changed from 67±31 mV, 84±14 mV to 413±71 mV, 305±47 mV. Also, the reduction and oxidation currents changed from 0.114±0.039 μA, −0.088±0.012 μA to 1.495±0.552 μA, −2.804±0.604 μA. Furthermore, the redox potentials of Fe ions changed from 67±31 mV, 84±14 mV to 349±52 mV, 374±55 mV. The reduction and oxidation currents changed from 0.114±0.039 μA, −0.088±0.012 μA to 1.361±0.192 μA, −1.958±0.249 μA. The reduction and oxidation potentials of Co ions changed from 67±31 mV, 84±14 mV to 320±59 mV, 350±34 mV. The reduction and oxidation currents changed from 0.114±0.039 μA, −0.088±0.012 μA to 1.338±0.262 μA, −1.493±0.356 μA. The reduction and oxidation potentials of Zn ions changed from 67±31 mV, 84±14 mV to 246±41 mV, 334±52 mV and the reduction and oxidation currents changed from 0.114±0.039 μA, −0.088±0.012 μA to 1.288±0.392 μA, −1.499±0.410 μA. In the case of the Ni(II) ions, the redox potential changed from 67±31 mV, 84±14 mV to 166±22 mV, 487±71 mV and the redox current also changed from 0.114±0.039 μA, −0.088±0.012 μA to 1.508±0.477 μA, −7.620±0.842 μA. FIG. **2*d*** shows this regulating effect. In the case of the Cu(II) ions, the redox potential changed from 67±31 mV, 84±14 mV to 106±27 mV, 275±34 mV and the redox current was changed from 0.114±0.039 μA, −0.088±0.012 μA to 2.384±0.415 μA, −2.287±0.356 μA. These results provide an easy method towards the regulation of electrochemical information depend on various input materials.

1.11. Information Reinforcement and Regulation

The current bioprocessing device was operated using a conventional 3 electrodes system for information regulation. All electrochemical measurements were performed in a Faraday cage. The recombinant azurin/DNA hybrid immobilized Au electrode was used as a working electrode. A Pt counter electrode and Ag/AgCl reference electrode were used for the electrochemical experiments, including cyclic voltammetry and chronoamperometry. The electrochemical experiments were performed with a CHI660A electrochemical workstation (CH Instruments, USA). All results were collected under ambient conditions. During each measurement, an N2 gas blanket was kept above the solution. Each voltammogram was scanned from the negative potential limit and increased to the positive potential limit at a scan rate of 50 $mVs^{-1}$.

1.12. Information Amplification

The scanning tunneling spectroscopy (STS) measurements were performed by Digital instruments Nanoscope® IV, USA at room temperature at a set point of 500 pA and 100 mV bias. The tunneling current being monitored by ramping the bias in the range of ±2.0 V. For the purpose of the electrical characterization at the nanoscale, the Au substrate was used as the bottom electrode, while the 14 mm conductive STM tip was used as the top electrode for both recombinant Az/DNA hybrid and recombinant Az/DNA-cDNA/nanoparticle hybrid sandwiched in between the contacts. The STS was performed by positioning the tungsten (W) tip over an isolated recombinant Az/DNA hybrid and recombinant Az/DNA-cDNA/nanoparticle hybrid after disabling the feedback control.

2. RESULTS AND DISCUSSION

To overcome this limitation of molecular electronics to develop a bioprocessing device, herein, for the first time we have designed a new bioprocessing device that can perform the various functions with a single hybrid molecule, derived from mere biomemory device with simple metalloprotein. The proposed bioprocessing device has the difference of 'versatile functionality' compared with the current silicon-based electronic devices. Usually, the organic-molecular based electronic device operates the simple function such as 'switching', 'On/Off', or 'In/Out' and these operations need integration of various components. However, the proposed bioprocessing device was mimicked their modulating function (biochemical inputs) that are coupled with enzyme system for biocatalyzing reactions which resembles to human brain organics, especially ""action-reaction" system. Biochemical reactions were observed as changes of bulk material properties or structural re-organizations at single molecule level can be demonstrated in machine language, thus allowing expression of the chemical processes in terms of computing operations instead of traditional chemistry materials transformations. The developed concept could be extended its notation to biohybrid molecular-based biocomputing system. Therefore, in this communication we developed bioprocessing device based on a single hybrid molecule, performing three different functions such as 'information reinforcement', 'information regulation' and 'information amplification'. These independent functions were originated from the interaction between redox properties of metalloprotein and commanding input materials. To perform these three functions on a single biohybrid material in bioelectronic device, we designed recombinant azurin/DNA (Az/DNA) hybrid molecule by using chemical ligation method (CLM). FIG. **3*a* shows the basic concept of memory modulating mechanism. This mechanism shows the interaction between redox property of metalloprotein and input materials and shown in FIG. 3*b***, is the recombinant azurin was utilized as memory platform where the DNA has a role of modulation operator. The modulation inputs can be, heavy metal ions or cDNA-conducting nanoparticles coupled to the hybrid molecule. This response on modulation input was measured by CV (cyclic voltammetry) and its application was investigated by CA (chronoamperometry). Finally, in the case of DNA-semiconducting nanoparticles as a modulation input, we confirmed the information amplification function by using STS (scanning tunneling spectroscopy).

2.1. Bioprocessing Device

The proposed bioprocessing device can easily assess and control various functions corresponding to the input materials in a confined region. Towards this, the prepared Azu/DNA hybrid was adsorbed on Au surface by self-assembly method. The Azu/DNA hybrid was conjugated by CLM. The conjugation method and film fabrication process were discussed in supplementary materials (FIG. 1). With SDS-PAGE analysis, the recombinant azurin-SMCC-DNA conjugation (Az/DNA hybrid) band corresponding to the predicted size of the recombinant azurin-SMCC-DNA conjugate was clearly visible on the gel (FIG. **3*c***, left). In case of recombinant azurin, the molecular weight (MW) is around 14.4 kDa and for ssDNA (52 mer) the MW is about 16.1 kDa but, the mw of recombinant azurin-SMCC-DNA conjugate was about 30.5 kDa. Thus, a highly pure recombinant Az/DNA conjugate formation was thus confirmed. Also, the recombinant azurin-SMCC-DNA conjugate concentration was determined by UV-Vis measurement at 260 nm (the absorbance coefficient of the conjugate, 260,000 $M^{-1}$ $cm^{-1}$). UV-Vis spectroscopy measurements were performed to analyze the recombinant azurin-SMCC-DNA conjugate. The *pseudomonas aeruginosa* azurin which is a blue copper metalloprotein was selected in this study. This blue copper protein coordinates five residues (Gly45, His46, Cys112, His117, Met121) and forms a unique geometry that gives rise to a unique absorption at 627 nm. In contrast, thiol-modified ssDNA does not have an intense absorption at 627 nm. But the recombinant azurin-SMCC-DNA conjugate, the recombinant azurin retained its geometry and the absorption at 627 nm was observed. FIG. 3*c* (right) shows the UV spectra of the recombinant azurin. Thus, the UV-Vis spectra can be used to assess successful bioconjugation. Based on this analysis, the recombinant azurin-SMCC-DNA hybrid was shown to be produced and retained its unique structure. Also, the fabrication method is well described in supplementary materials (Fabrication session). FIG. 3*d* shows the AFM image of Az/DNA hybrid, and FIG. 3*e* shows the Raman analysis of Az/DNA hybrid self-assembled layer. The detailed description of AFM and Raman analysis were explained in supplementary materials (AFM, Raman Spectroscopy section).

2.2. Cyclic Voltammetry Method

Figure 6A:
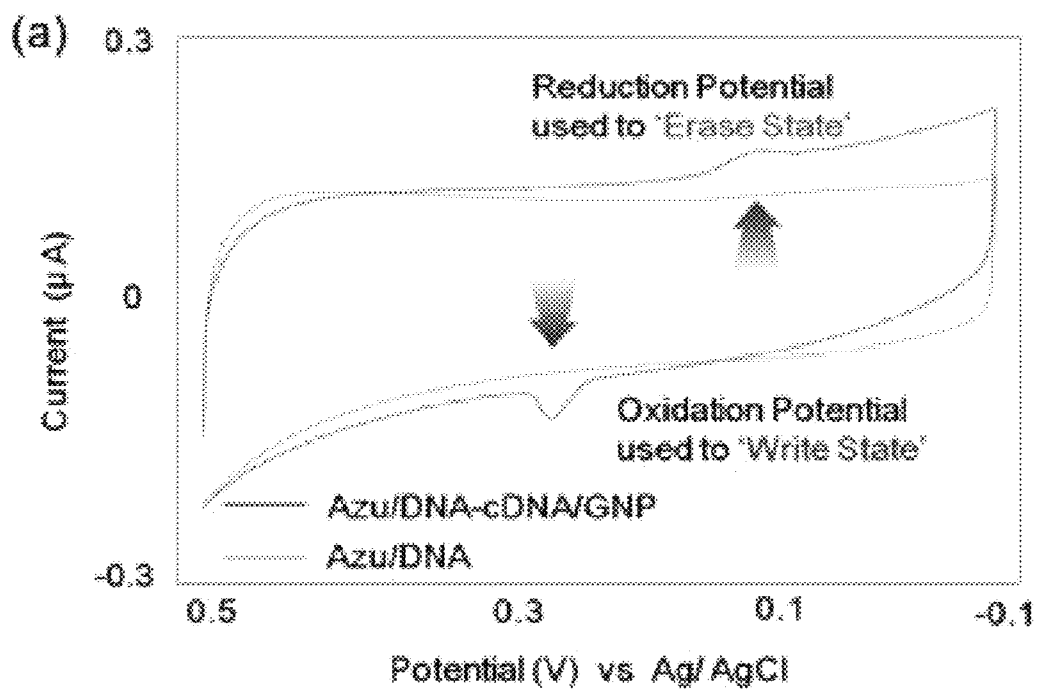
FIGS. 6*a* to 6*f* illustrate an information reinforcement function of a recombinant azurin/DNA hybrid.

The concept of information reinforcement was originated from electrochemical-based 2-state biomemory. Basically, the 2-state biomemory was operated by two input parameters, the oxidation potential and reduction potential which were obtained from cyclic voltamogram. Hence, to figure out these values CV measurements were conducted. FIG. 6*a* depicts the CV results of 1) Azu/DNA hybrid, and 2) Azu/DNA-cDNA/GNP hybrids. The reduction and oxidation potentials of Azu/DNA hybrid are 67±31 mV, 84±14 mV. The obtained results clearly shows the signal enhancement in the redox property when cDNA-GNP was added to Azu/DNA molecule. The values of oxidation and reduction potentials were found to be 232±39 mV, 83±68 mV. Furthermore, the redox properties of 3 different biomolecules were investigated as a control group (recombinant azurin, thiol-modified ssDNA, Azu/DNA hybrid). The results are described in supplementary materials and it is shown in FIG. 4 and Table 2.

TABLE 2

| | Potential | |
|---|---|---|
| | Reduction Potential (mV) | Oxidation Potential (mV) |
| Recombinant Azurin | 159 ± 23 | 242 ± 22 |
| ssDNA | 93 ± 19 | 292 ± 26 |
| Azurin-DNA | 67 ± 31 | 84 ± 14 |
| | Current | |
| | Reduction Current ($10^{-7}$ A) | Oxidation Current ($10^{-7}$ A) |
| Recombinant Azurin | 1.783 ± 0.281 | −2.124 ± 0.455 |
| ssDNA | 1.264 ± 0.377 | −1.761 ± 0.263 |
| Azurin-DNA | 1.140 ± 0.394 | −0.877 ± 0.123 |

Figure 6B:
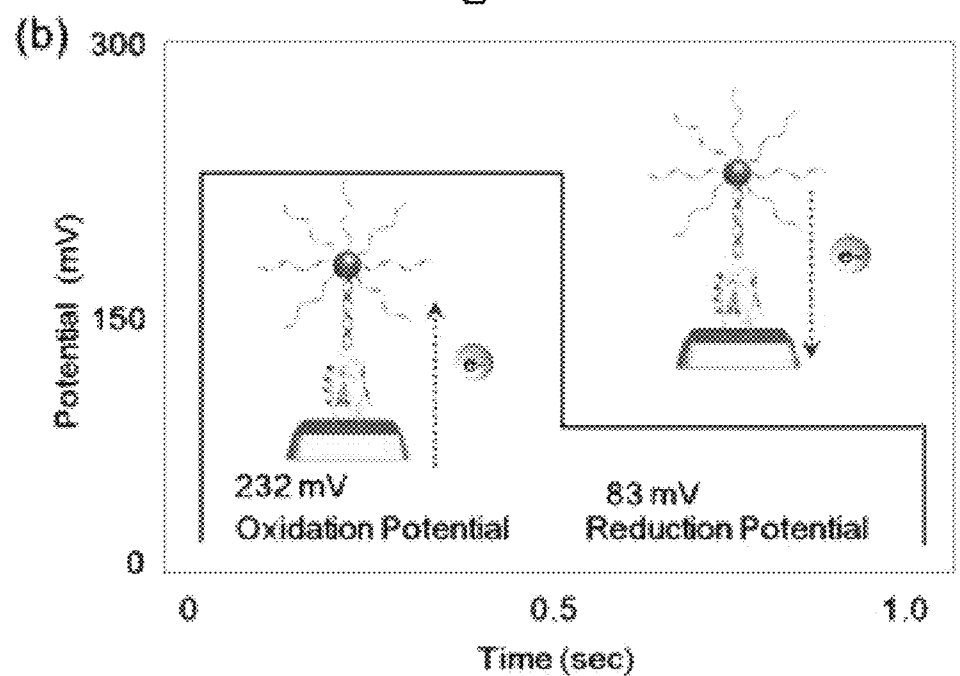
Figure 6C:
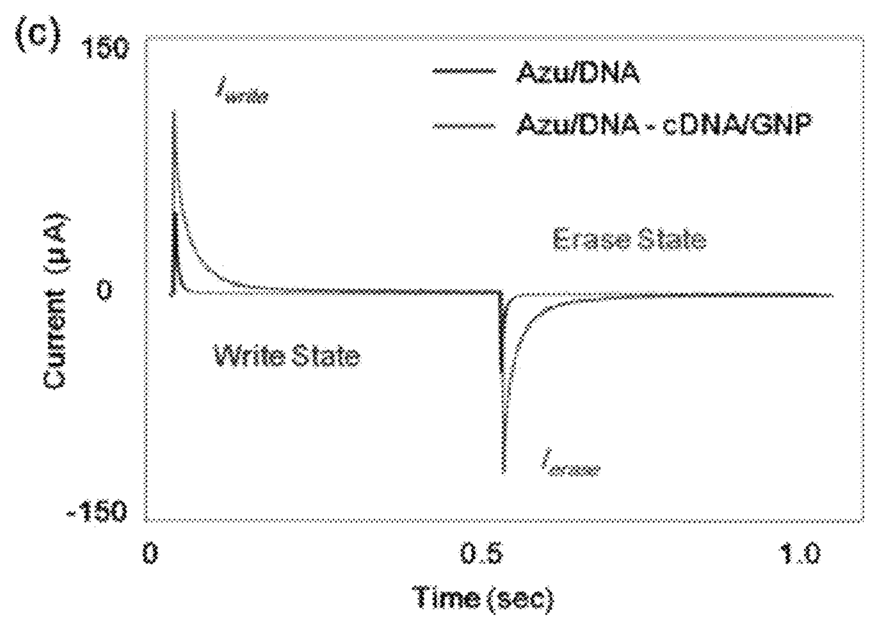

To assess the information reinforcement performance, the chronoamperometry (CA) method was used to validate the information storage function. The CA enabled to apply the measured oxidation potential (OP) and reduction potential (RP) to prepared working electrode which results in the faradaic current transitions for both oxidation and reduction potentials indicating that the device can be switched ON and OFF states for charge storage functions. Using this approach, the OP and RP can be applied to working electrodes which were obtained from previous CV experiments. Upon application of OP, the potential gives the electron transfer from the Azu/DNA hybrid to the electrode leads the storage of positive charge. This state can be regarded as Write'state. The application of RP enables to produce an outflow of electron transfer to the Azu/DNA hybrid and this state also can be regarded as 'Erase' state. Applying OP, RP and measuring the current response depend on the resistance-capacitance (RC) time constant of the electrochemical system. As shown in FIG. 6*b*, OP step of 232 mV quantitatively oxidizes the Azu/DNA hybrid layer (write state), resulting in the storage of positive charge in biohybrid and the application of a RP of 83 mV converted the layer into its original form (erase state), where the reductive current had a magnitude equal to the oxidation current. FIG. 6*c* shows the two types of currents responses in which OP step of 232 mV and RP of 83 mV were applied to the recombinant azurin/DNA hybrid layer, the conventional biomemory function was validated (FIG. 6*c*: black line). Here, the function of information reinforcement was similar to the conventional biomemory function. However, when the cDNA-GNP was added to Azu/DNA hybrid, the performance considering charge storage capability was drastically enhanced compared to conventional biomemory device at defined area (FIG. 6*c*: purple line). These characteristics we can define it as the 'information reinforcement' at one single biohybrid molecule.

With these currents values, the stored charge value with Azu/DNA hybrid was easily estimated from Eq. (1).

$$Q=\int idt \quad (1)$$

Figure 6D:
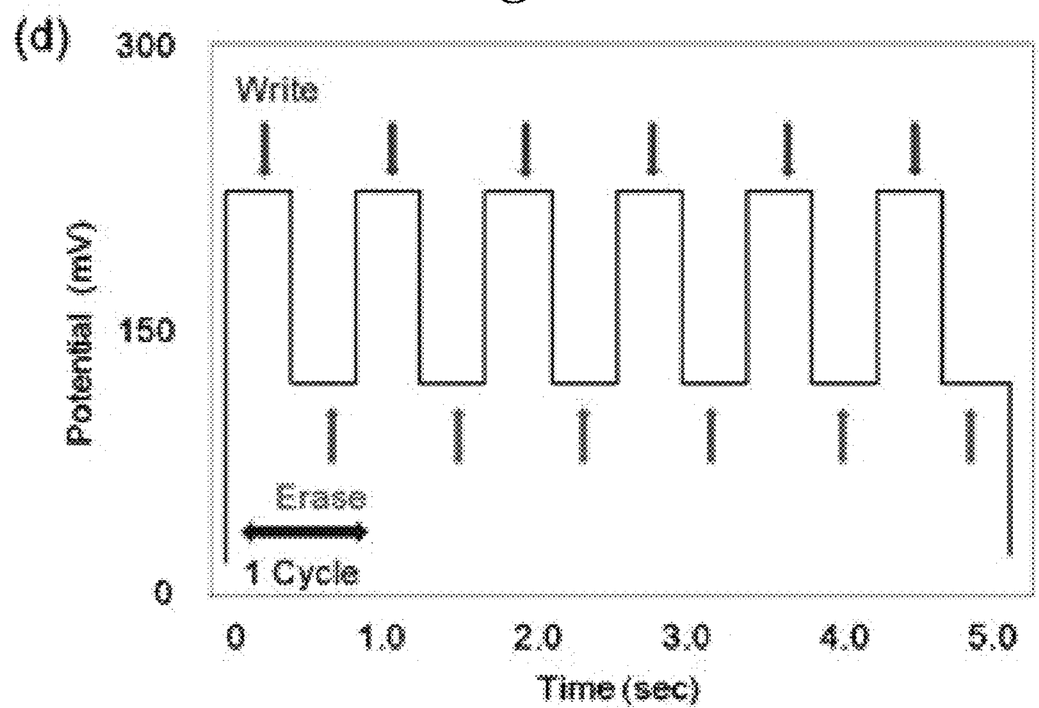
Figure 6E:
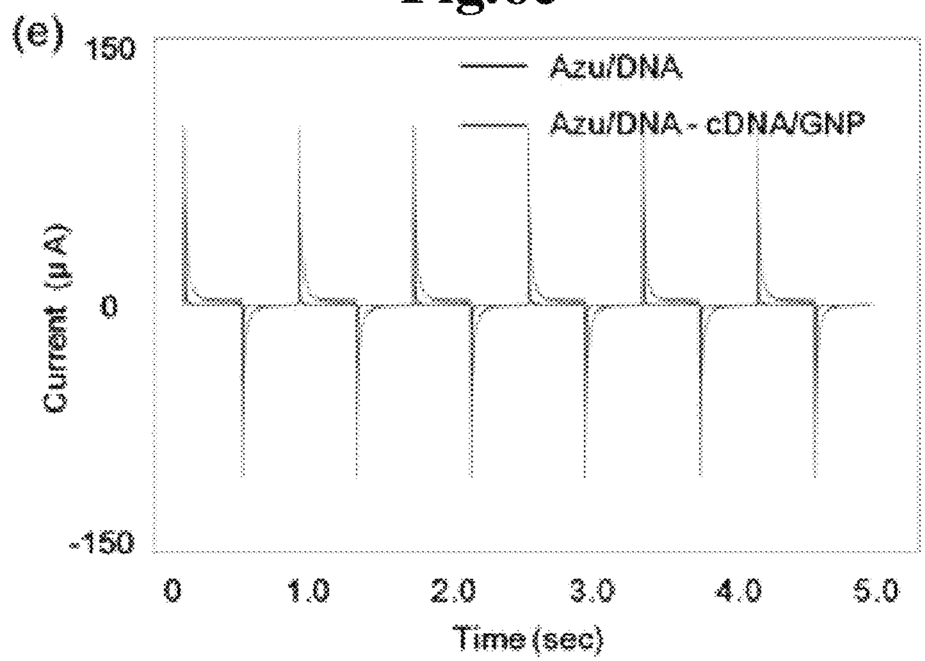
Figure 6F:
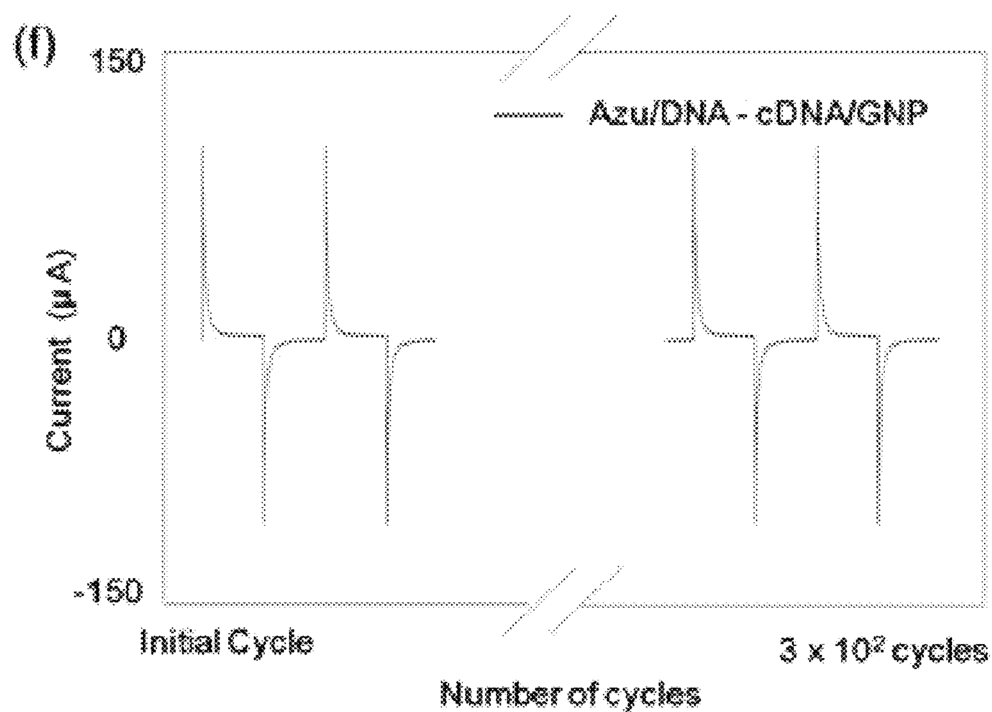

The amount of charge stored to Azu/DNA hybrid by writing or erasing was calculated from the currents of CA which is found to be $5.328\times10^{-7}$ C. Similarly, the charge stored at Azu/DNA-cDNA/GNP was calculated to be $\approx4.636\times10^{-6}$ C. These results can be translated that the charging capacity of Azu/DNA-cDNA/GNP was incremented approximately by 870% compared to Azu/DNA hybrid. Presumably, this result was observed when biomolecules are coupled with nanoparticles to form a bionano hybrid, the energy levels were mixed which favors the possibility of for higher energy transfer phenomena. Several groups already reported a energy level mixing and its electron transfer effect when biomolecule were conjugated to nanoparticles. Thus, this phenomenon was resulted from donor-bridge-acceptor system considering electron transfer across the biomolecule-conducting nanoparticle interface. This mechanism was well described in supplementary materials. With this mechanism, the information storage function can established and this function was examined continuously for 6 cycles (12 steps). FIG. 6*d*, 6*e* show the schematic diagram of OP, RP application and its current response. In this context, we can regard as the more charged current from application of OP, RP to information value of '1' and '0'. Moreover, FIG. 6*f* also shows memory performance which maintained for 300 cycles. The results demonstrated stability and repeatability of proposed information storage function. The results present here we can easily control the information reinforcement of Azu/DNA-cDNA/GNP hybrid. This phenomena was inferred to the conducting nanoparticle is powerful input material for information reinforcement in bioprocessing device. As a result, the first bioprocessing function was well established.

2.3. Information Regulation

Figures 7A, 7B:
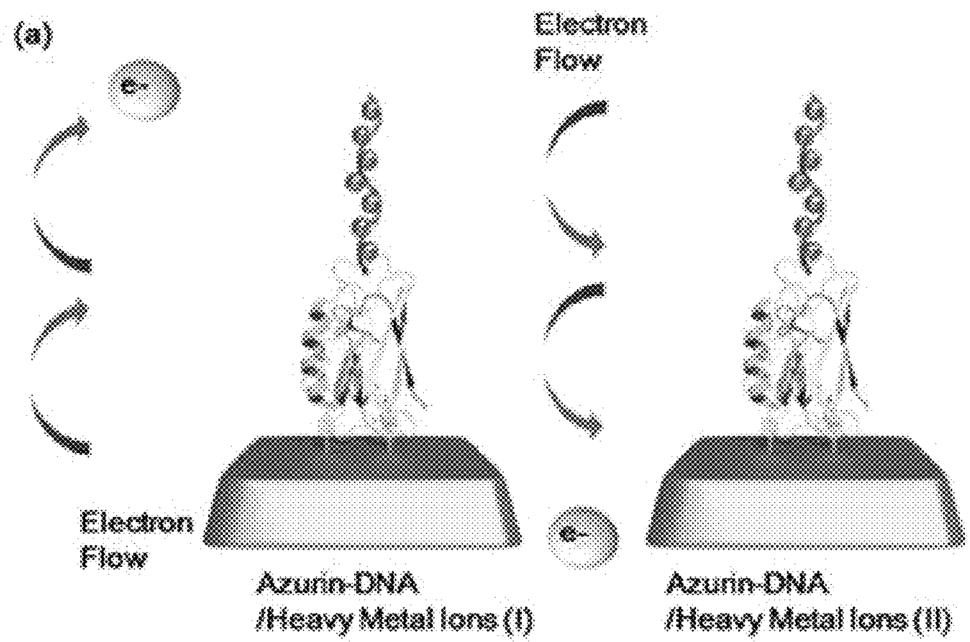
FIGS. 7*a* to 7*d* illustrate an information regulation function of a recombinant azurin/DNA hybrid.

To prove information regulation mechanism, various input materials were added to react with Azu/DNA hybrid to get the output information. With the obtained values, we can regulate the information corresponding to metal ions. To perform information regulation, the ssDNA component was used as the modulation operator. Because the ssDNA arm of Azu/DNA has a high selective binding to its complementary ssDNA (cDNA) molecule, in this study, the cDNA can be a powerful tool for various applications. The ssDNA arm has a charged backbone that can bind to various heavy metal ions, such as Cu, Zn, Ni, Co, Fe, Mn (FIG. 7*a*). Thus, the ssDNA arm can use as a regulating receptor, where the input materials, such as heavy metal ions, can be regarded as the modulating operator. DNA molecules has been shown to contain four potential sites for binding with metal ions, 1) the negatively charged phosphate oxygen atoms, 2) the ribose hydroxyls, 3) the base ring and 4) exocyclic base keto groups. Evidently, the interaction between DNA and the heavy metal ions during electron transfer play an essential role in modulating and processing the electrochemical signals. Also, the effect of Cu(II) and Ni(II) compounds on dsDNA was previously investigated to better understand their interactions with base donor systems. Further, the electrochemical behavior of biomolecules was observed to vary in accordance with the presence of coordinated metal ions, such as Ni(II), Co(II), Mn(II), which is located at the center of the azurin molecule. In this context, we assumed that the different input materials, such as heavy metal ions, would strongly affect the electrochemical properties of the Azu/DNA hybrid.

Figure 7C:
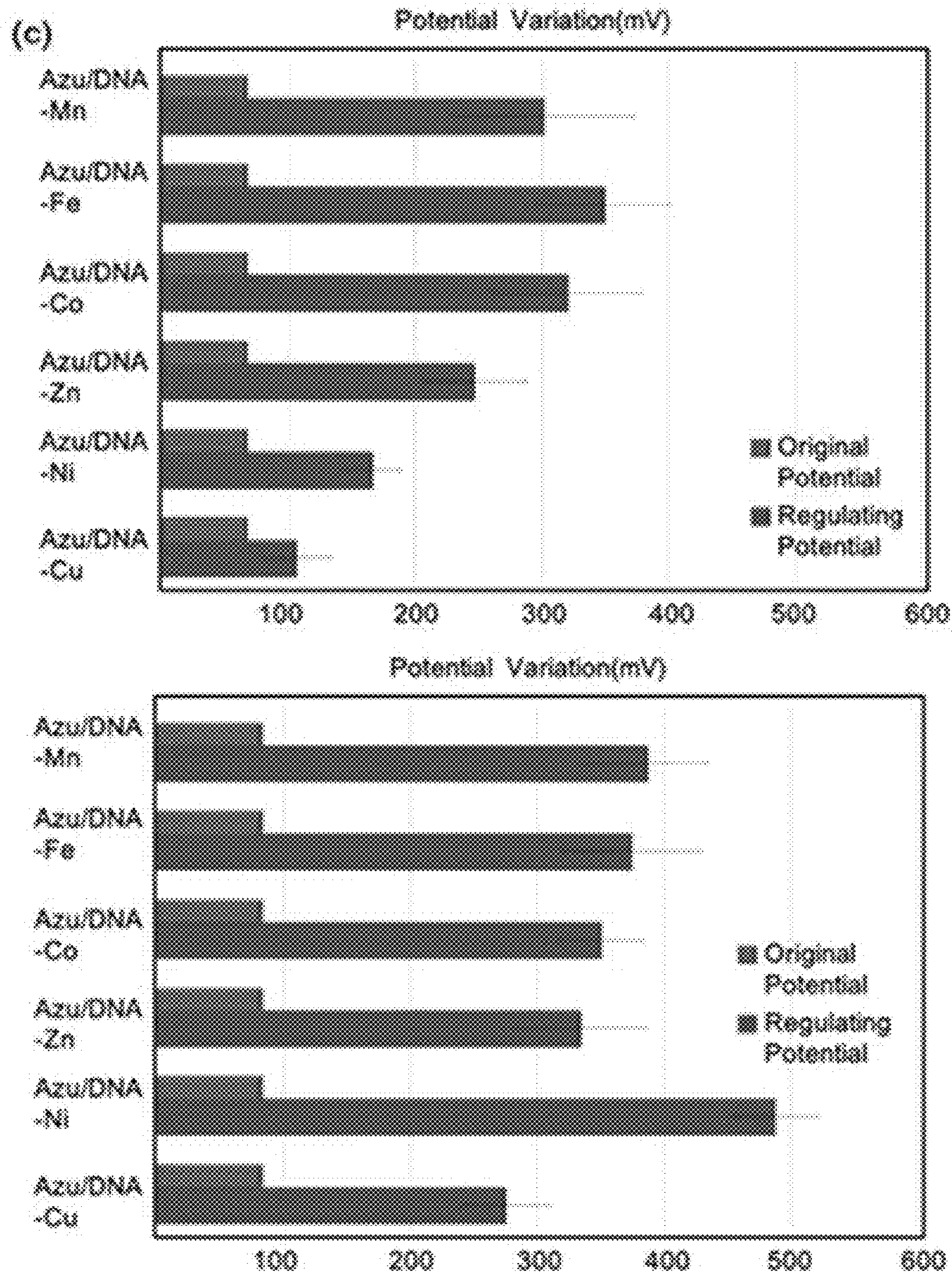

The reduction and oxidation potentials of the Mn ions changed from 67±31 mV, 84±14 mV to 413±71 mV, 305±47 mV. Also, the redox potentials of Fe ions changed from 67±31 mV, 84±14 mV to 349±52 mV, 374±55 mV. The reduction and oxidation potentials of Co ions changed from 67±31 mV, 84±14 mV to 320±59 mV, 350±34 mV. The reduction and oxidation potentials of Zn ions changed from 67±31 mV, 84±14 mV to 246±41 mV, 334±52 mV. In the case of the Ni(II) ions, the redox potential changed from 67±31 mV, 84±14 mV to 140±22 mV, 437±71 mV. In the case of the Cu(II) ions, the redox potential changed from 67±31 mV, 84±14 mV to 106±27 mV, 275±34 mV. All values of redox potentials are listed in FIG. 7*b*. The obtained OP and RP were used to memory regulating parameters. Also, the cyclic voltamogram of each case of redox potentials specified are in supplementary materials (FIG. 5). FIG. 7*c* describes the potential variation values of Az/DNA hybrid when various input materials, such as heavy metal ions were added. FIG. 7*c* explains the reduction potential regulation when various input materials added respectively. Also, FIG. 7*c* explains the oxidation potential regulation when various input materials added compared to oxidation potential value of Azu/DNA hybrid.

Figure 7D:
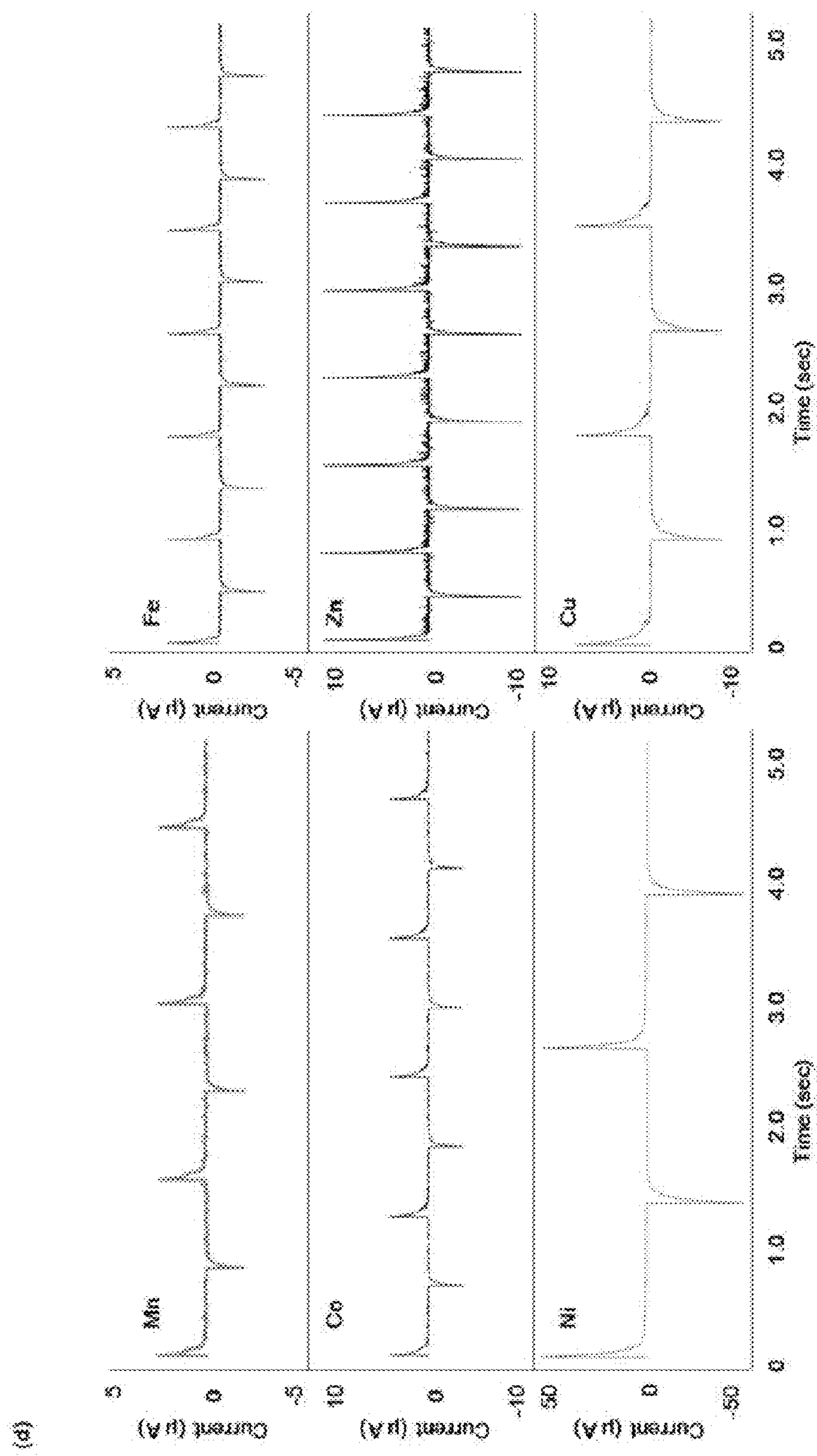

With these regulation parameters, we can control the memory regulation by CA method. FIG. 7*d* depicts the regulated bioprocessing device according to input heavy metal ions. When, 413 mV of OP and 305 mV of RP are applied to the Azu/DNA-Mn hybrid repeatedly, the electron was stored and erased was observed for a duration of 5 sec. FIG. 7*d* (yellow line) shows its current response. Particularly, the application of OP enables to charge the 0.37±0.12 μC of electron was stored at a time approximately. And, when 374 mV of OP was applied to the Azu/DNA-Fe hybrid layer, then, 0.51±0.13 μC of electron was stored at a time. The application of 349 mV of RP was erased their information. This memory regulation step was repeated 6 times (FIG. 7*d*). Moreover, if 350 mV and 320 mV of OP, RP applied to the Azu/DNA-Co hybrid, then 0.56±0.28 μC of electron was charged and discharged during 5 sec (FIG. 7*d*). Similarly, the Azu/DNA-Zn hybrid layer was used to memory regulation function by application of OP (334 mV, RP 246 mV), respectively. Then, 1.59±0.41 μC of electron was regulated (FIG. 7*d*) and this charge switching was repeated 7 times. In case of the Azu/DNA-Ni hybrid (OP: 437 mV, RP: 140 mV, FIG. 7*d*: green line), the Azu/DNA-Cu hybrid (OP: 275 mV, RP: 106 mV, FIG. 7*d*) layers are regulated corresponding to their redox potentials. Then, the modulated currents are 4.10±0.59 μC and 1.33±0.34 μC, respectively. Thus the electrochemical information regulation can be realized into various applications such as bioelectrochemical transducer, heavy metal ion detecting biosensors, biological-based battery device and a platform for understanding behavior between protein/DNA hybrid and metal ions. Simply, the proposed bioprocessing system composed of protein/DNA hybrid shows the memory regulation function according to various heavy metal ions with easy method.

2.4. Information Amplification

Figure 8A:
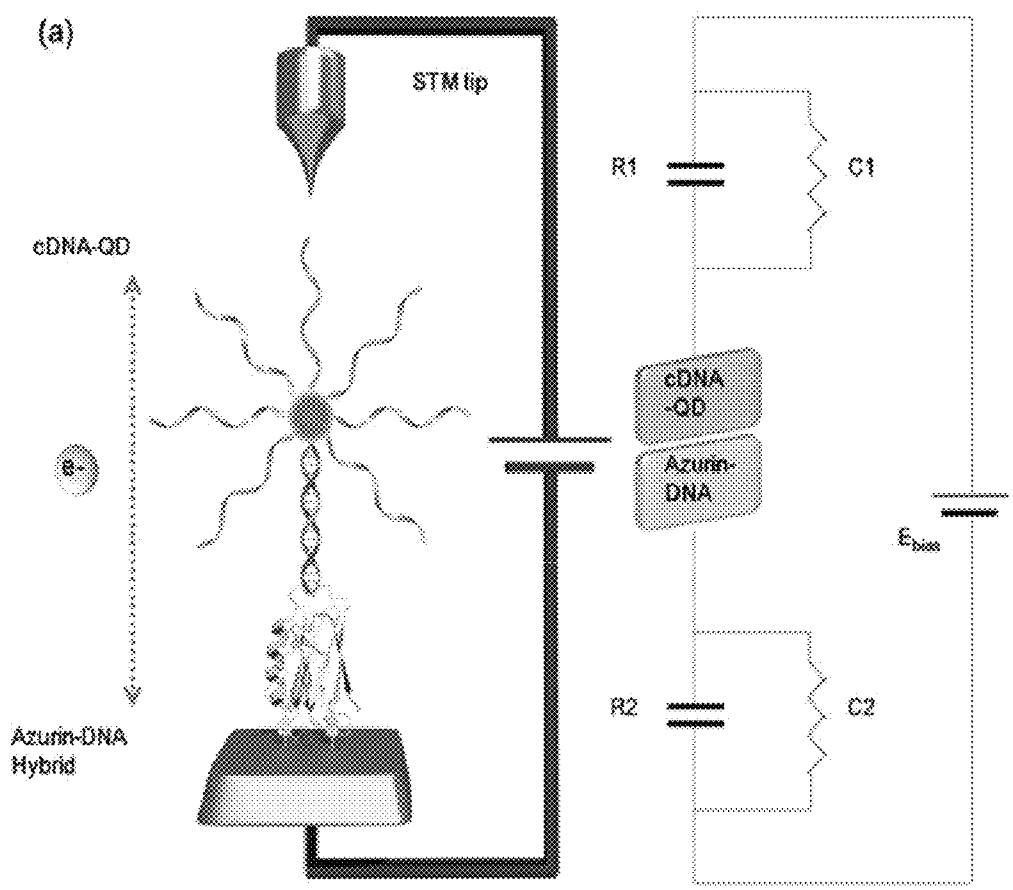
FIGS. 8*a* to 8*d* illustrate an information amplification function of a recombinant azurin/DNA hybrid.
Figure 8B:
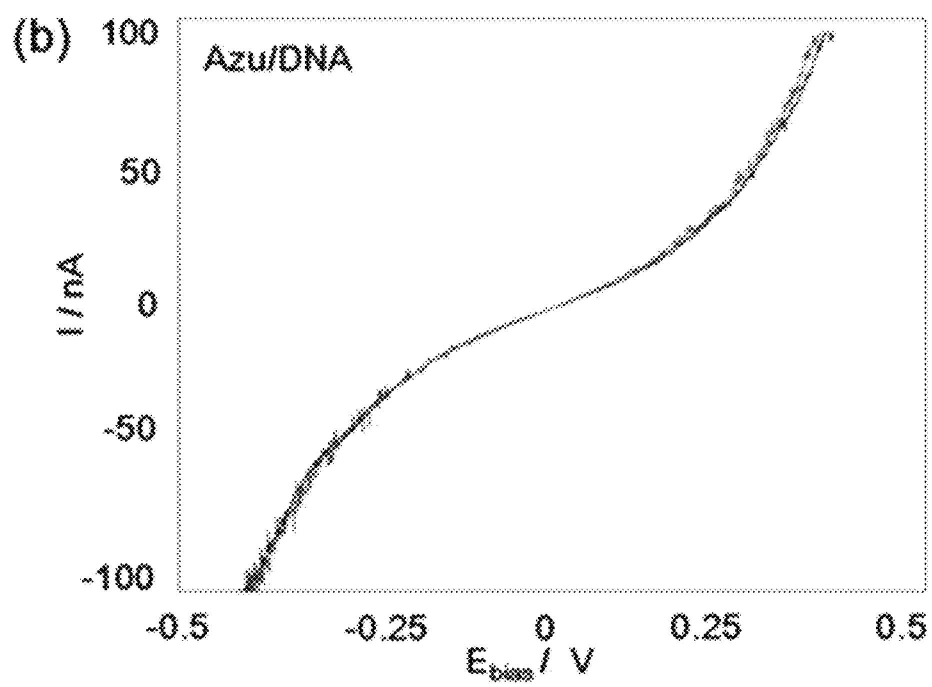
Figure 8C:
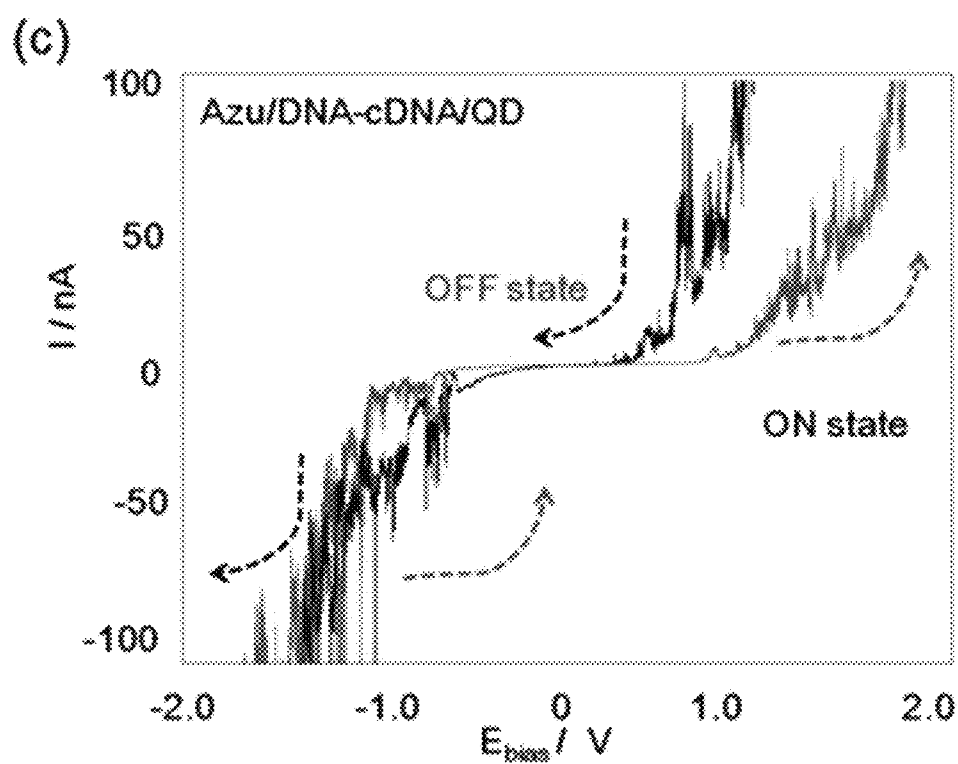

For validating information amplification function, we conducted scanning tunneling spectroscopy measurements on Azu/DNA hybrid and Azu/DNA hybrid/biotin-tagged cDNA coupled with streptavidin-coated CdSe—ZnS (Azu/DNA-cDNA/QD) immobilized on Au surface. As STM is capable of high-spatial-resolution measurements, we have collected I-V data at several points on Azu/DNA hybrid molecules and Azu/DNA-cDNA/QD hybrid. Our measurements show there is a little difference in the I-V curves of Azu/DNA hybrid, indicating that electron tunneling is occurring via whole molecule. FIG. 8*a* shows the set-up composition of scanning tunneling spectroscopy (STS) which is an effective tool for the information amplification through Azu/DNA hybrid in the double-barrier tunnel-junction (DBTJ) configuration. Here, a DBTJ was realized by positioning the STM tip over the Azu/DNA hybrid which depicted in FIG. 8*a*. The tunneling conductance across the junction can be measured by various potentials. Moreover, the capacitance and tunneling resistance of the tip-Azu/DNA hybrid junction ($C_1$ and $R_1$) can be easily manipulated by changing the tip hybrid distance, which is usually achieved by controlling the STM bias and current settings ($V_s$ and $I_s$). On the other hand, the Azu/DNA hybrid junction parameters ($C_2$ and $R_2$) are practically stable. By varying $C_1$, one can modify the single electron charging energy, EC, which depends on the capacitance values, as well as the voltage distribution between the two junctions, which is determined by the capacitance ratio, $V_1/V_2=C_2/C_1$. FIG. 8*b* shows an application of bias voltage from −0.5 to +0.5 V on the Azu/DNA hybrid depicts the semiconductor behavior, as after 0.2 V of applied bias, the Azu/DNA hybrid shows a non-ohmic behavior and behaves like a diode. However, FIG. 8*c* shows the characteristics of Azu/DNA-cDNA/QD hybrid under the application of −2.0 to +2.0 V which shows electrical bistability. The range of voltage-scan was kept small so as to ensure that the scanning does not itself induce a higher conducting state. As observed, the Azu/DNA-cDNA/QD hybrid is initially in a low conducting state (defined as OFF state) until it reaches about 0.8 V where are an abrupt change i.e., increase in the current occurs (defined as ON state), indicating a transition of the conjugate from an initial OFF state to ON state, equivalent to the writing process in a digital memory device. When a negative voltage is applied, the conjugate returned to low conductivity state (OFF state) when a bias voltage equivalent to erase state of the device which is approximately −0.8 V. This change in transition from low to high conductivity is because of the charge donor azurin which transfers the electron due to Cu (I) and Cu (II) densities of states through tunneling to the lower energy core of CdSe—ZnS core-shell nanoparticle. It is assumed that free electrons will tunnel through the conjugate by forming a double tunnel junction which has distribution of many energy levels sandwiched between the two metal electrodes. When applied bias is high enough, the free electrons will tunnel through the barriers, leading to a polarization with respect to Au and Pt electrodes. As a result, the proposed bioprocessing device undergoes a dramatic change of conductance for information amplification. If the applied bias is removed, the polarized charges cannot recombine, thus the device remains in the high-conductance state, where only a reverse bias can recover the device.

Figure 8D:
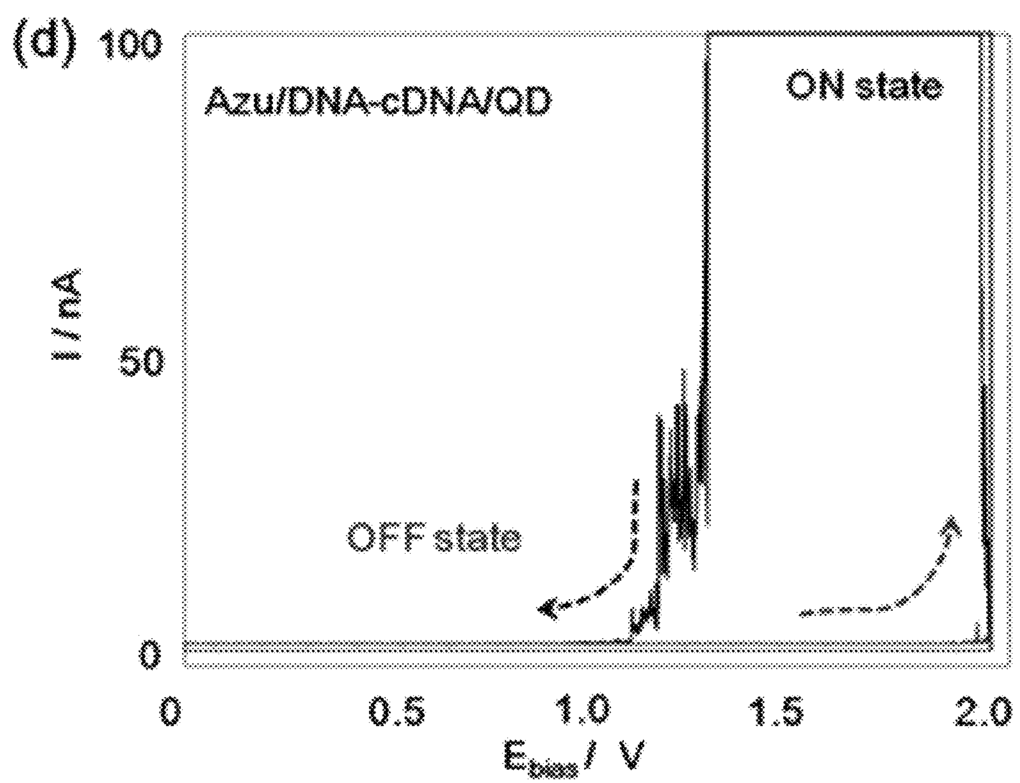

Moreover, I-V characteristics of a monolayer of Az/DNA-cDNA/QD hybrid core-shell nanoparticles, measured with a Pt/Ir tip of a STM under two sweep voltage directions, are shown in FIG. 4*d* under the application of 0-2-0 V. It is clearly observed that the device switches to its high (ON) state with as sharp increase in the injection current at about 2 V indicating the transition of the device from the low conductivity state (OFF state) to a high conductivity state (ON state). This transition from the OFF state to the ON state is equivalent to the 'writing' process in a digital memory cell and this transition can be defined as 'information amplification'. One of the most important features of our Az/DNA-cDNA/QD is that the OFF state can be recovered by the simple application of a reverse voltage pulse. This is equivalent to the 'erasing' process of a digital memory cell. FIG. 8*d* shows the I-V characteristics of the device after the application of a revere bias; the device switched from high conductive state to low conductive state at 1.1 V. This bistable behavior, the OFF-ON transitions, and the creation of nonvolatile information amplification effects can be observed only in the presence of the hybrid molecules between the metal electrodes. Here, the hybrid conjugate acts as a carrier blocking material, resulting in the blockage of electrons due to the relatively large energy barrier between the work function of Au electrode and the HOMO level of the hybrid layer. When a positive applied voltage is applied to the electrode, after the injection of electrons from the Pt/Ir tip into the LUMO level occurs through the Fowler-Nordheim tunneling process, the electrons existing at the LUMO level are transported among the hybrid molecules along the direction of the applied bias voltage through the tunneling process. This results in the achievement of the writing process. When a negative voltage is applied to the electrode, because the electrons captured in the valence band of Azu/DNA-cDNA/QD under the negative electric field are and then transported to the Pt/Ir electrode through the Fowler-Nordheim tunneling process, the erasing process is performed. This is equivalent to the erasing process of a digital memory cell. Like this, we have carried out information amplification function with Azu/DNA-cDNA/QD. In this context, the third function of bioprocessing device was well developed.

3. CONCLUSION

In this study, for the first time we presented a novel bio-inspired bioprocessing device composed of protein/DNA/nanoparticle hybrid that could reinforce, regulate and amplify information in single hybrid biomolecule. The significance of proposed device goes beyond a totally conceptual advance in the molecular-scale biocomputing field. At first, the proposed bioprocessing device was operated with information reinforce function. This function enables to store more charge compared to conventional biomemory device. Second, the information regulation can assess the various potentials which depend on input materials. This regulation function can provide the application such as multi-bit biomemory. Third, information amplification can be applied to solid-state biotransistor. These results suggested that the proposed approach based on information control using single hybrid biomolecule encompasses the bioprocessor concept which can perform the multi-function in single molecule. It is usually difficult to generalize with biomolecules because of their simple characteristics and intrinsic problems, including their simple function in storing different information. However, the device presented here should be viewed as a model which provides us multi-functions at single hybrid biomolecule. A combination of these results will pave the way to our ambitious goal such as biocomputing system in a single hybrid biomolecule.

4. REFERENCES

[1] Y. Cui, C. M. Lieber, *Science* 2001, 291, 851.

[2] S.-J. Liu, P. Wang, Q. Zhao, H.-Y. Yang, J. Wong, H.-B. Sun, X.-C. Dong, W.-P. Lin, W. Huang, *Adv. Mater* 2012, 24, 2901.

[3] C. M. Lieber, W. Lu, *Nat. Mater.* 2010, 6, 841.

[4] A. M. Mahmoud, A. J. Bergren, N. Pekas, R. L. McCreery, *Adv. Fund. Mater.* 2011, 21, 2273.

[5] H. Song, M. A. Reed, T. Lee, *Adv. Mater* 2011, 23, 1583.

[6] K. Moth-Poulsen, T, Bjørnholm, *Nat. Nanotechol.* 2009, 4, 551.

[7] R. R. Birge, N. B. Gillespie, E. W. Izaguirre, A. Kusnetzow, A. F. Lawrence, D. Singh, Q. W. Song, E. Schmidt, J. A. Stuart, *J. Phys. Chem.* B 1999, 103, 10746.

[8] A. Noy, *Adv. Mater.* 2011, 23, 807.

[9] B. H. Robinson, N. C. Seeman, *Protein Eng.* 1987, 1, 295.

[10] F. C. Simmel, *ACS Nano* 2013, 7, 6.

[11] J.-W. Choi, B.-K. Oh, J. Min, Y. J. Kim, *Appl. Phys. Lett.* 2007, 91, 263902.

[12] T. Lee, S.-U. Kim, J. Min, J.-W. Choi, *Adv. Mater.* 2010, 22, 510.

[13] T. Lee, S.-U. Kim, J. Min, J.-W. Choi, *Biomaterials* 2011, 32, 3815.

[14] A. K. Yagati, T. Lee, J. Min, J.-W. Choi, *Biosens. Bioelectron.* 2013, 40, 283.

[15] H. Gu, J. Chao, S.-J. Xiao, N. C. Seeman, *Nature* 2010, 465, 202.

[16] G. D. Ruiter, M. E. Van der Boom, *Acc. Chem. Res.* 2011, 44, 563.

[17] M. Amrute-Nayak, R. P. Diensthuber, W. Steffen, D. Kathmann, F. K. Hartmann, R. Fedorov, C. Urbanke, D. J. Manstein, B. Brenner, G. Tsiavaliaris, Angew. Chem. Int. Ed. 2010, 49, 312.

[18] P. N. Bartlett, *Bioelectrochemistry: Fundamentals, Experimental Techniques and Applications*. Wiley, UK 2008, p. 424.

[19] T. Pawlowski, J. Swiatek, K. Gasiorowski, H. Kozlowski, *Inorg. Chem. Acta.* 1987, 136, 185.

[20] P. Bhyrappa, M. Sankar, B. Varghese, *Inorg. Chem.* 2006, 45, 4136.

[21] I. Delfino, S. Cannistraro, *Biophys. Chem.* 2009, 139, 1.

[22] D. Katz, O. Millo, S. Kan, U. Banin, *Appl. Phys. Lett.* 2001, 79, 117.

Although the present invention has been described in detail with reference to the specific features, it will be apparent to those skilled in the art that this description is only for examples of the present invention and does not limit the scope of the present invention. These embodiments are only for illustrating the present invention more specifically, and it is apparent to those skilled in the art that the scope of the present invention is not limited by these embodiments.

The invention claimed is:

1. A self-assembled monolayer comprising a hybrid of (a) azurin; and (b) a single strand DNA (ssDNA) in the 30-mer to 70-mer size range conjugated to azurin, wherein azurin is a recombinant protein in which a cysteine residue is introduced, the recombinant protein being directly immobilized onto a substrate through the cysteine residue, and wherein the ssDNA is conjugated to azurin via a linker.

2. The self-assembled monolayer of claim 1, wherein the ssDNA is modified with a thiol group, and conjugated to azurin via linker.

3. The self-assembled monolayer of claim 2, wherein the linker is sulfosuccinimidyl-4-(N-maleimidomethyl) cyclohexane-1-carboxylate (SMCC), formaldehyde, 1-ethyl-3-[3-dimethylaminopropyl]carbodiimide hydrochloride (EDC), bis[beta-(4-azidosalicylamido)ethyl]disulfide) (BASED), or bis-maleimidohexane (BMH).

4. The self-assembled monolayer of claim 1, wherein the self-assembled monolayer is operated by application of a reduction potential and an oxidation potential.

5. The self-assembled monolayer of claim 1, further comprising conductive nanoparticles, semi-conducting nanoparticles, or heavy metal ions.

6. The self-assembled monolayer of claim 5, wherein a DNA sequence complementary to the ssDNA is coupled with the nanoparticles.

7. The self-assembled monolayer of claim 5, wherein the heavy metal ions bind to the ssDNA through ionic bonds.

8. The self-assembled monolayer of claim 5, wherein the self-assembled monolayer has a function of information reinforcement, information regulation, or information amplification.

9. A method for fabricating the self-assembled monolayer of claim 1, the method comprising:

(a) preparing a hybrid by conjugating azurin to ssDNA; and (b) immobilizing the hybrid onto a substrate.

10. The method of claim 9, wherein the ssDNA is modified with a thiol group, and conjugated to the protein having a redox potential via a linker.

11. The method of claim 10, wherein the linker is sulfosuccinimidyl-4-(N-maleimidomethyl) cyclohexane-1-carboxylate (SMCC), formaldehyde, 1-ethyl-3-[3-dimethylaminopropyl]carbodiimide hydrochloride (EDC), bis[beta-(4-azidosalicylamido)ethyl]disulfide) (BASED), or bis-maleimidohexane (BMH).

12. The method of claim 9, wherein the ssDNA is in the 20-mer to 100-mer size range.

13. The method of claim 9, wherein the hybrid is prepared by:

(a) modifying the ssDNA with a thiol group to prepare thiol-modified ssDNA;

(b) reacting the thiol-modified ssDNA with a linker to prepare a thiol-modified ssDNA-linker; and (c) conjugating the thiol-modified ssDNA-linker to the azurin.

14. The method of claim 9, wherein the self-assembled monolayer is operated by application of a reduction potential and an oxidation potential.

15. The method of claim 9, wherein the self-assembled monolayer further comprises conductive nanoparticles, semi-conducting nanoparticles, or heavy metal ions.

16. The method of claim 15, wherein a DNA sequence complementary to the ssDNA is coupled with the nanoparticles.

17. The method of claim 15, wherein the heavy metal ions bind to the ssDNA through an ionic bond.

18. The method of claim 15, wherein the self-assembled monolayer has a function of information reinforcement, information regulation, or information amplification.

* * * * *

SEQUENCE LISTING

```
<160> NUMBER OF SEQ ID NOS: 2

<210> SEQ ID NO 1
<211> LENGTH: 52
<212> TYPE: DNA
<213> ORGANISM: Artificial Sequence
<220> FEATURE:
<223> OTHER INFORMATION: Synthetic Construct

<400> SEQUENCE: 1

cccgggaaaa cccgggtttt cccgggaaaa cccgggtttt cccgaaaaaa aa              52


<210> SEQ ID NO 2
<211> LENGTH: 16
<212> TYPE: DNA
<213> ORGANISM: Artificial Sequence
<220> FEATURE:
<223> OTHER INFORMATION: Synthetic Construct

<400> SEQUENCE: 2

aaccaacctt tttttt                                                      16
```